US012233146B2

(12) United States Patent
Guerard et al.

(10) Patent No.: US 12,233,146 B2
(45) Date of Patent: Feb. 25, 2025

(54) PROCESS FOR DYEING KERATIN FIBERS USING A DIRECT DYE AND A SACCHARINATE SALT AND COMPOSITION COMPRISING THEM

(71) Applicant: L'Oreal, Paris (FR)

(72) Inventors: Olivier Guerard, Aulnay-Sous-Bois (FR); Stéphane Sabelle, Aulnay-Sous-Bois (FR)

(73) Assignee: L'OREAL, Paris (FR)

( * ) Notice: Subject to any disclaimer, the term of this patent is extended or adjusted under 35 U.S.C. 154(b) by 72 days.

(21) Appl. No.: 18/012,206

(22) PCT Filed: Jun. 18, 2021

(86) PCT No.: PCT/EP2021/066704
§ 371 (c)(1),
(2) Date: Dec. 21, 2022

(87) PCT Pub. No.: WO2021/259809
PCT Pub. Date: Dec. 30, 2021

(65) Prior Publication Data
US 2023/0346669 A1    Nov. 2, 2023

(30) Foreign Application Priority Data

Jun. 22, 2020 (FR) ...................... 2006513

(51) Int. Cl.
*A61Q 5/10* (2006.01)
*A61K 8/35* (2006.01)
*A61K 8/49* (2006.01)

(52) U.S. Cl.
CPC .............. *A61K 8/494* (2013.01); *A61K 8/355* (2013.01); *A61K 8/49* (2013.01); *A61Q 5/10* (2013.01); *A61K 2800/4324* (2013.01); *A61K 2800/882* (2013.01)

(58) Field of Classification Search
CPC .......... A61K 8/494; A61K 8/355; A61K 8/49; A61K 2800/4324; A61K 2800/882; A61K 8/35; A61K 8/411; A61K 8/418; A61K 8/44; A61K 8/4946; A61K 2800/432; A61Q 5/10; A61Q 5/065
USPC .......................................................... 8/405
See application file for complete search history.

(56) References Cited

U.S. PATENT DOCUMENTS

| | | | |
|---|---|---|---|
| 3,524,842 A | 8/1970 | Grossmann et al. | |
| 3,578,386 A | 5/1971 | Kalopissis et al. | |
| 3,617,163 A | 11/1971 | Kalopissis et al. | |
| 3,817,698 A | 6/1974 | Kalopissis et al. | |
| 3,869,454 A | 3/1975 | Lang et al. | |
| 3,955,918 A | 5/1976 | Lang | |
| 4,025,301 A | 5/1977 | Lang | |
| 4,886,517 A | 12/1989 | Bugaut et al. | |
| 5,708,151 A | 1/1998 | Möckli | |
| 5,798,095 A | 8/1998 | Racky | |
| 5,879,413 A | 3/1999 | Pengilly et al. | |
| 5,888,252 A | 3/1999 | Möckli | |
| 5,919,273 A | 7/1999 | Rondeau et al. | |
| 5,993,490 A | 11/1999 | Rondeau et al. | |
| 6,045,591 A | 4/2000 | Deneulenaere | |
| 6,136,042 A | 10/2000 | Maubru | |
| 6,179,881 B1 | 1/2001 | Henrion et al. | |
| 6,458,167 B1 | 10/2002 | Genet et al. | |
| 6,797,013 B1 | 9/2004 | Lang et al. | |
| 7,998,223 B2 * | 8/2011 | Asada .................. | A61Q 5/10 8/408 |
| 8,088,177 B2 * | 1/2012 | Sasao .................. | A61K 8/86 8/405 |
| 8,088,178 B2 * | 1/2012 | Sasao .................. | A61K 8/86 8/405 |
| 8,834,580 B2 * | 9/2014 | Goettel ................ | A61Q 5/10 8/405 |
| 2004/0214339 A1 | 10/2004 | Profitt et al. | |
| 2011/0229425 A1 * | 9/2011 | Sasao .................. | A61K 8/86 8/405 |
| 2011/0302726 A1 | 12/2011 | Beyer et al. | |
| 2012/0207689 A1 * | 8/2012 | Konno ................. | A61K 8/046 8/405 |
| 2014/0082856 A1 | 3/2014 | Goettel et al. | |
| 2014/0283315 A1 * | 9/2014 | Matsutani ............ | A61K 8/86 8/405 |
| 2016/0158130 A1 * | 6/2016 | Mori .................... | A61K 8/35 8/405 |
| 2018/0021600 A1 * | 1/2018 | Kobayashi ........... | A61K 8/49 8/405 |

FOREIGN PATENT DOCUMENTS

| | | | | |
|---|---|---|---|---|
| CN | 1520517 A | | 8/2004 | |
| DE | 2527638 A1 | | 5/1976 | |
| DE | 2538363 A1 | | 5/1976 | |
| DE | 4137005 A1 | | 5/1993 | |
| DE | 4220388 A1 | | 12/1993 | |
| DE | 102010043497 A1 * | | 9/2011 | ............. A61Q 5/10 |

(Continued)

OTHER PUBLICATIONS

STIC Search Report dated Apr. 3, 2024.*
Seidler et al., "The qualification of different ditetrazolium salts as indicators in the oxido-reductase histochemistry," Acta histochem, Bc. 61 (1), (1978), pp. 48-52.
Alberti et al., "Ricerche Sui Coloranti Cationici Per Fibra Acrilica," La Chimica E L'Industria, vol. 56, No. 9, Sep. 1974, pp. 600-602.
Savarino et al., "Disperse and Cationic Dyes from Aminophenyl-X-Azolo-Pyridines," Dyes and Pigments 11 (1989), pp. 163-172.
Viscardi, Guido et al., "Disperse Cationic Azo Dyes from Heterocyclic Intermidiaties," Dyes and Pigments, vol. 19, No. 1, (1992), pp. 69-79.
Neidlein, Richard et al., "Synthese von Substituierten Pyridiniumsalzen," German Monatshefte für Chemie, (1975), vol. 106, No. 3, pp. 643-648 (English translation unavailable).

(Continued)

Primary Examiner — Eisa B Elhilo
(74) Attorney, Agent, or Firm — THE MARBURY LAW GROUP, PLLC

(57) ABSTRACT

The present invention relates to a process for dyeing keratin fibers using a) one or more direct dyes and b) one or more particular saccharinate salts.

20 Claims, No Drawings

(56) References Cited

FOREIGN PATENT DOCUMENTS

| | | | | |
|---|---|---|---|---|
| DE | 102017211645 A1 | 1/2019 | | |
| EP | 0714954 A2 | 6/1996 | | |
| EP | 0850636 A1 | 7/1998 | | |
| EP | 0850637 A1 | 7/1998 | | |
| EP | 0860636 A1 | 8/1998 | | |
| EP | 0918053 A1 | 5/1999 | | |
| EP | 0920856 A1 | 6/1999 | | |
| EP | 1062940 A1 | 12/2000 | | |
| EP | 1133975 A2 | 9/2001 | | |
| EP | 1133976 A2 | 9/2001 | | |
| EP | 3047842 A1 | * 7/2016 | ............... | A61Q 5/10 |
| FR | 1221122 A | 5/1960 | | |
| FR | 1476584 A | 4/1967 | | |
| FR | 1516943 A | 2/1968 | | |
| FR | 1540423 A | 9/1968 | | |
| FR | 1560664 A | 3/1969 | | |
| FR | 1567219 A | 5/1969 | | |
| FR | 2189006 A1 | 1/1974 | | |
| FR | 2275462 A1 | 1/1976 | | |
| FR | 2285851 A1 | 4/1976 | | |
| FR | 2570946 A1 | 4/1986 | | |
| FR | 2757385 A1 | 6/1998 | | |
| FR | 2788433 A1 | 7/2000 | | |
| GB | 738585 A | 10/1955 | | |
| GB | 1097269 A | 1/1968 | | |
| GB | 1163385 A | 9/1969 | | |
| GB | 1195386 A | 6/1970 | | |
| GB | 1514466 A | 6/1978 | | |
| JP | 2005053821 A | * 3/2005 | ............... | A61K 7/13 |
| JP | 2011132192 A | 7/2011 | | |
| KR | 20040079800 A | 9/2004 | | |
| WO | 95/01772 A1 | 1/1995 | | |
| WO | 95/15144 A1 | 6/1995 | | |
| WO | 9606544 A1 | 3/1996 | | |
| WO | 97/44004 A1 | 11/1997 | | |
| WO | 99/48465 A1 | 9/1999 | | |
| WO | 01/66646 A1 | 9/2001 | | |
| WO | 03/029359 A1 | 4/2003 | | |

OTHER PUBLICATIONS

Zhousheng et al., "Research and Application of the Coordination Reaction of New Fluorescent Reagent CCPAR and CU(II)," Huazue Fence, vol. 29, No. 4, (1993), pp. 233-234.
Balaban et al., "Reactions of Pyrylium Salts with Nucleophiles, XX. Synthesis of 4-(N-Pyridinium)-4'-DialkylaminoAzobenzene and of 4-(4-Dialkylaminophenylazo)-4'-(N-Pyridinium)-Biphenyl Derivatives," Revue Roumaine de Chimie, 33, (1988), pp. 377-383.
Alberti et al., "Thermodynamic Features in Acrylic Fiber Dyeing with Basic Dyes," Textile Research Institute, 54(2), Feb. 1984, pp. 105-107.
Stashkevich et al., "Bisformazans and bistetrazolium salts, derivatives of quinaldine quaternary salts," Zhurnal Obshchei Khimii (1970), 40(1), pp. 195-202 (partial GB translation).
Yen, et al., "The Design and Synthesis of Bisazo Series Compound Used in Organophotoconductor," MRL Bull. Res. Dev., vol. 6, No. 2 (1992), pp. 21-27.
Kuznetsova et al., "The determination of Thickness of a Histological Section by Interference Microscopy," Tsitologiya, vol. 10, No. 3, (1968), pp. 403-405.
Tien, Hsien-Ju et al., "Syntheses of New Azo Dyestuff Containing a Sydnone Ring," Journal of the Chinese Chemical Society, (Taipei), (1998), 45(1), pp. 209-211.
International Search Report and Written Opinion for counterpart Application No. PCT/EP2021/066704, dated Aug. 30, 2021.
Translation of Office Action in JP2022578718, mailed Dec. 25, 2023, 8 pages.
Office Action in CN202180043750.5, mailed Feb. 6, 2024, 15 pages.

* cited by examiner

PROCESS FOR DYEING KERATIN FIBERS USING A DIRECT DYE AND A SACCHARINATE SALT AND COMPOSITION COMPRISING THEM

CROSS REFERENCE TO RELATED APPLICATIONS

This is a National Stage Application of PCT/EP2021/066704, filed internationally on Jun. 18, 2021, which claims priority to French Application No. 2006513, filed on Jun. 22, 2020, the contents of both of which are incorporated by reference herein in their entireties.

FIELD OF THE INVENTION

The present invention relates to a process for dyeing keratin fibers using a) one or more direct dyes and b) one or more particular saccharinate salts.

BACKGROUND OF THE INVENTION

It is known practice to dye keratin fibers and in particular human hair with dye compositions containing oxidation dye precursors, which are generally known as oxidation bases, such as ortho- or para-phenylenediamines, ortho- or para-aminophenols and heterocyclic compounds. These oxidation bases are generally combined with couplers. These bases and couplers are colorless or weakly colored compounds, which, when combined with oxidizing products, may give rise to colored compounds by a process of oxidative condensation. This type of oxidation dyeing makes it possible to obtain "permanent" colorings.

Moreover, it is known practice to dye keratin fibers and in particular human hair with dye compositions containing direct dyes. The standard dyes that are used are, in particular, dyes of the nitrobenzene, anthraquinone, nitropyridine, azo, xanthene, acridine, azine or triarylmethane type, or natural dyes. These dyes are colored or coloring molecules that have affinity for keratin fibers.

Compositions containing one or more direct dyes are applied to the keratin fibers for a time necessary to obtain the desired coloring, and are then rinsed out. The resulting colorings are particularly chromatic colorings, but are, however, temporary or semi-permanent since the nature of the interactions that bind the direct dyes to the keratin fiber and their desorption from the surface and/or the core of the fiber are responsible for their weaker dyeing power and their poorer persistence with respect to washing or perspiration.

Direct dyeing products notably make it possible to modify the natural color of the hair, or to cover white hairs. However, the intensity of the coloring obtained by using these products is occasionally judged as being too weak relative to the expectations of users on the day of application.

In addition, direct colorings have the drawback of fading out over time, in particular under the action of UV, inclement weather and successive shampooing.

There is therefore a real need to develop a process for dyeing keratin fibers using direct dyes which makes it possible to obtain a better color build-up and intense and chromatic colors.

The applicant has discovered, surprisingly, that all of these objectives can be achieved by the process according to the present invention.

SUMMARY OF THE INVENTION

According to a first aspect, a subject of the present invention is a process for dyeing keratin fibers using:

a) one or more direct dyes; and
b) one or more compounds of formula (A):

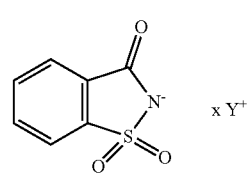

wherein:
$Y^+$ represents a cationic counterion chosen from the compounds of formula (Ia), (Ib), (Ic) or (Id) below:

formula (Ia) wherein $R_1$, $R_2$, $R_a$ and $R_4$ represent independently of one another:
a hydrogen atom;
a linear or branched, saturated or unsaturated, $C_1$-$C_{12}$, preferably $C_1$-$C_{10}$, hydrocarbon-based group, optionally substituted with one or more group(s) chosen from: hydroxyl, thiol, ($C_1$-$C_6$)alkylthio, amino, —$NH_3^+$, ($C_1$-$C_6$)dialkylamino, ($C_1$-$C_5$)alkylamino, ($C_1$-$C_4$)alkoxyl, carboxyl, carboxylate, —$SO_3H$, —$SO_3^-$, —$C(O)NH_2$, —NHC(NH)—$NH_2$, —$C(O)OR^a$, —OC(O)—$R^a$, —$C(O)NHR^a$, —NH—C(O)—$R^a$, phenyl, indolyl, phenol, furan, guaiacol, imidazole or guanine and/or optionally interrupted by one or more group(s) chosen from —C(O)—, —$NR^b$—, —$C(NR^b)$—, —OC(O)—, —C(O)O—, —$C(O)NR^b$— or —$NR^bC(O)$—;
$R^a$ representing a ($C_1$-$C_4$)alkyl group; and
$R^b$ representing a hydrogen atom or a ($C_1$-$C_4$)alkyl group, preferably a hydrogen atom; it being understood that the overall charge of the compounds of formula (Ia) is positive;

formula (Ib) wherein:
X represents an oxygen atom or an $NR^b$ group;
$R_5$, $R_6$ and $R_7$ represent independently of one another:
a hydrogen atom;
a carboxyl or carboxylate group;
a —$C(O)NH_2$ group;
a linear or branched, saturated or unsaturated, $C_1$-$C_{12}$, preferably $C_1$-$C_{10}$, hydrocarbon-based group, optionally substituted with one or more group(s) chosen from: hydroxyl, thiol, ($C_1$-$C_6$)alkylthio, amino, —$NH_3^+$, ($C_1$-$C_6$)dialkylamino, ($C_1$-$C_5$)alkylamino, ($C_1$-$C_4$)alkoxyl, carboxyl, carboxylate, —$SO_3H$, —$SO_3^-$, —$C(O)NH_2$, —NHC(NH)—$NH_2$, —$C(O)OR^a$, —OC(O)—$R^a$, —$C(O)NHR^a$, —NH—C(O)—$R^a$, phenyl, indolyl, phenol, furan, guaiacol, imidazole or guanine and/or optionally interrupted by one or more group(s) chosen from —C(O)—, —NR$^b$—, —C(NR$^b$)—, —OC(O)—, —C(O)O—, —C(O)NR$^b$— or —NR$^b$C(O)—;

R$^a$ representing a (C$_1$-C$_4$)alkyl group; and

R$^b$ representing a hydrogen atom or a (C$_1$-C$_4$)alkyl group, preferably a hydrogen atom;

it being understood that the overall charge of the compounds of formula (Ib) is positive;

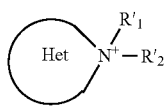

(Ic)

formula (Ic) wherein:

Het represents a cationic saturated heterocyclic group comprising:

from 5 to 10 ring members, preferably 5 or 6 ring members; and in addition to the ammonium bearing R'$_1$ and R'$_2$, optionally one or two atoms chosen from nitrogen and/or oxygen atoms, preferably a nitrogen atom;

the heterocyclic group being optionally substituted with one or more group(s) R'$_3$;

R'$_1$ and R'$_2$, which may be identical or different, represent a hydrogen atom or a linear or branched, saturated or unsaturated, C$_1$-C$_{12}$ hydrocarbon-based group, optionally substituted with one or more group(s) chosen from: hydroxyl, amino, (C$_1$-C$_6$)dialkylamino, (C$_1$-C$_6$)alkylamino, carboxyl, carboxylate, carbamide, (C$_1$-C$_4$) alkoxyl, —SO$_3$H, —SO$_3^-$ or phenyl;

R'$_3$, which may be identical or different, represent a hydroxyl group, an amino group, a —C(O)OR'$_4$ group, an —OC(O)—R'$_4$ group, a —C(O)NHR'$_4$ group, an —NH—C(O)—R'$_4$ group, a linear or branched, saturated or unsaturated, C$_1$-C$_{12}$ hydrocarbon-based group, optionally substituted with one or more group(s) chosen from: hydroxyl, amino, (C$_1$-C$_6$)dialkylamino, (C$_1$-C$_6$)alkylamino, carboxyl, carboxylate, carbamide, (C$_1$-C$_4$)alkoxyl, —SO$_3$H, —SO$_3^-$ or phenyl;

R'$_4$ represents a hydrogen atom, a linear or branched, saturated or unsaturated, C$_1$-C$_{12}$ hydrocarbon-based group, optionally substituted with one or more group(s) chosen from hydroxyl, amino, (C$_1$-C$_6$)dialkylamino or (C$_1$-C$_6$)alkylamino;

it being understood that the overall charge of the compounds of formula (Ic) is positive;

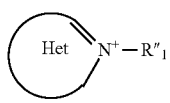

(Id)

formula (Id) wherein:

Het' represents a cationic aromatic unsaturated heterocyclic group comprising:

from 5 to 10 ring members, preferably 5 or 6 ring members; and in addition to the ammonium bearing R"$_1$, optionally one or two atoms chosen from nitrogen or oxygen atoms, preferably a nitrogen atom;

said heterocyclic group being optionally substituted with one or more group(s) R"$_2$;

R"$_1$ represents a linear or branched, saturated or unsaturated, C$_1$-C$_{12}$ hydrocarbon-based group, optionally substituted with one or more group(s) chosen from hydroxyl, amino, (C$_1$-C$_6$)dialkylamino, (C$_1$-C$_6$)alkylamino, carboxyl, carboxylate, carbamide, (C$_1$-C$_4$) alkoxyl, —SO$_3$H, —SO$_3^-$ or phenyl; and R"$_2$, which may be identical or different, represent a hydroxyl group, an amino group, or a linear or branched, saturated or unsaturated, C$_1$-C$_{12}$ hydrocarbon-based group, optionally substituted with one or more group(s) chosen from hydroxyl, amino, (C$_1$-C$_6$) dialkylamino, (C$_1$-C$_6$)alkylamino, carboxyl, carboxylate, carbamide, (C$_1$-C$_4$)alkoxyl, —SO$_3$H, —SO$_3^-$ or phenyl;

it being understood that the overall charge of the compounds of formula (Id) is positive;

x is a stoichiometric coefficient chosen so as to ensure the electrical neutrality of the compound of formula (A);

it being understood that the ingredients a) and b) are applied simultaneously or sequentially to the keratin fibers, preferably simultaneously.

According to a second aspect, a subject of the present invention is a composition comprising:

a) optionally one or more direct dyes; and b) one or more compounds of formula (A) as defined above.

According to a third aspect, a subject of the present invention is a multicompartment device or kit, comprising a first compartment which comprises one or more direct dyes and a second compartment which comprises one or more compounds of formula (A) as defined above.

DETAILED DESCRIPTION OF THE INVENTION

For the purposes of the present invention and unless otherwise indicated:

the term "keratin fibers" is intended to mean fibers of human or animal origin such as head hair, bodily hair, the eyelashes, the eyebrows, wool, angora, cashmere or fur.

According to the present invention, the keratin fibers are preferably human keratin fibers, more preferentially the hair;

the term "direct dyes" is intended to mean natural and/or synthetic dyes, including in the form of an extract or extracts, other than oxidation dyes. These are dyes that will spread superficially on the fiber. They may be ionic or nonionic, i.e. anionic, cationic, neutral or nonionic. The direct dyes may be of the same types of ionicity or else as mixtures.

the direct dyes contain one or more chromophores, and these dyes are capable of absorbing light at a wavelength $\lambda_{abs}$ ranging from 400 nm to 700 nm;

the fluorescent direct dyes are dyes containing at least one fluorescent chromophore, and these dyes are capable of absorbing in the visible range at a wavelength $\lambda_{abs}$ ranging from 400 nm to 800 nm and of re-emitting in the visible range at a wavelength $\lambda_{em}$ longer than that absorbed ranging from 400 nm to 800 nm.

The difference between the absorption and emission wavelengths, also known as the Stoke's shift, is from 1 nm to 100 nm. Preferably, the fluorescent direct dyes are dyes that are capable of absorbing at a wavelength $\lambda_{abs}$ ranging from 420 nm to 550 nm and of re-emitting in the visible range at a wavelength $\lambda_{em}$ ranging from 470 to 600 nm;

the term "alkyl group" is intended to mean a linear or branched, saturated hydrocarbon-based radical;

the term "($C_x$-$C_y$)alkyl group" means an alkyl group comprising from x to y carbon atoms;

the term "hydroxy($C_x$-$C_y$)alkyl group" is intended to mean a ($C_x$-$C_y$)alkyl group, at least one of the hydrogen atoms of which is replaced with a hydroxyl (—OH) group;

the term "(hydroxy)($C_x$-$C_y$)alkyl group" is intended to mean a hydroxy($C_x$$C_y$)alkyl group or a ($C_x$-$C_y$)alkyl group;

the term "alkoxy group" means an alkyl group bonded to an oxygen atom;

the term "($C_x$-$C_y$)alkoxy group" means an alkoxy group comprising from x to y carbon atoms;

the term "hydroxy($C_x$-$C_y$)alkoxy group" is intended to mean a ($C_x$-$C_y$)alkoxy group, at least one of the hydrogen atoms of which is replaced with a hydroxyl (—OH) group;

the expression "optionally substituted" applied to an alkyl or alkoxy group implies that the alkyl or alkoxy group may be substituted with one or more groups chosen from: i) hydroxyl, ii) ($C_1$-$C_4$) alkoxy, iii) acylamino, iv) amino optionally substituted with one or two identical or different (hydroxy)($C_1$-$C_4$)alkyl groups, said alkyl groups possibly forming, with the nitrogen atom that bears them, a heterocycle comprising from 5 to 7 ring members, said heterocycle optionally comprising another nitrogen or non-nitrogen heteroatom; v) a quaternary ammonium group —N$^+$R'R"R'", M$^-$ for which R', R" and R'", which may be identical or different, represent a hydrogen atom or a ($C_1$-$C_4$)alkyl group, or else R', R" and R'" form, with N$^+$, a heteroaryl such as imidazolium optionally substituted with a ($C_1$-$C_4$)alkyl group, and M$^-$ represents an anion, or a mixture of anions, intended to ensure electrical neutrality;

the term "alkylene group" is intended to mean a linear or branched $C_1$-$C_{10}$, particularly $C_1$-$C_6$, more particularly $C_1$-$C_2$, acyclic hydrocarbon-based divalent chain, optionally substituted with one or more groups, which may be identical or different, chosen from i) hydroxyl, ii) ($C_1$-$C_2$)alcoxyl, iii) (poly)hydroxy($C_2$-$C_4$)alcoxy(di)($C_1$-$C_2$)(alkyl)amino, iv) (poly)hydroxy(di)($C_1$-$C_2$)(alkyl)amino, v) $R^a$—$Z^a$—$C(Z^b)$—$Z^c$—, vi) $R^a$—$Z^a$—$C(Z^b)$—$Z^a$— and vii) $R^a$—$Z^a$—$S(O)_t$—$Z^c$— with $Z^a$ and $Z^b$, which may be identical or different, representing an oxygen or sulfur atom, or a group NR$^{a'}$, $Z^c$, representing a bond, an oxygen or sulfur atom, or a group NR$^a$; $R^a$ representing an alkali metal, a hydrogen atom or an alkyl group, or else is absent if another part of the molecule is cationic, and $R^{a'}$ representing a hydrogen atom or an alkyl group and t is equal to 1 or 2; preferably the "alkylene group" represents a —(CH$_2$)$_p$— group with p being an integer between 1 and 6, preferably between 1 and 4;

the term "(hetero)aryl" is intended to mean an aryl group or a heteroaryl group;

the term "aryl group" is intended to mean a monocyclic or fused or non-fused polycyclic carbon-based group, comprising from 6 to 22 carbon atoms, at least one ring of which is aromatic; preferably, the aryl group is a phenyl, biphenyl, naphthyl, indenyl, anthracenyl or tetrahydronaphthyl;

the term "heteroaryl group" is intended to mean an optionally cationic, 5- to 22-membered monocyclic or fused or non-fused polycyclic group, comprising from 1 to 6 heteroatoms chosen from nitrogen, oxygen, sulfur and selenium atoms, and at least one ring of which is aromatic; preferentially, a heteroaryl group is chosen from acridinyl, benzimidazolyl, benzobistriazolyl, benzopyrazolyl, benzopyridazinyl, benzoquinolyl, benzothiazolyl, benzotriazolyl, benzoxazolyl, pyridinyl, tetrazolyl, dihydrothiazolyl, imidazopyridinyl, imidazolyl, indolyl, isoquinolyl, naphthoimidazolyl, naphthooxazolyl, naphthopyrazolyl, oxadiazolyl, oxazolyl, oxazolopyridyl, phenazinyl, phenoxazolyl, pyrazinyl, pyrazolyl, pyrilyl, pyrazoyltriazyl, pyridyl, pyridinoimidazolyl, pyrrolyl, quinolyl, tetrazolyl, thiadiazolyl, thiazolyl, thiazolopyridinyl, thiazoylimidazolyl, thiopyrylyl, triazolyl, xanthylyl and its ammonium salt;

a (hetero)aryl group or the aryl or heteroaryl part of a group may optionally be substituted with at least one group borne by a carbon atom, chosen from:

a ($C_1$-$C_{10}$)alkyl, preferably ($C_1$-$C_3$)alkyl, group, optionally substituted with at least one group chosen from: hydroxyl, ($C_1$-$C_2$)alkoxy, hydroxy($C_2$-$C_4$)alkoxy, acylamino, amino optionally substituted with one or two ($C_1$-$C_4$)alkyl groups, which may be identical or different, optionally bearing at least one hydroxyl group, or the two ($C_1$-$C_4$)alkyl groups possibly forming, with the nitrogen atom to which they are attached, a 5- to 7-membered and preferably 5- or 6-membered heterocycle, said heterocycle being saturated or unsaturated and optionally substituted and optionally comprising another nitrogen or non-nitrogen heteroatom;

a halogen atom;

a hydroxyl group;

a ($C_1$-$C_2$)alkoxy group;

a hydroxy($C_2$-$C_4$)alkoxy group;

an amino group;

a 5- or 6-membered heterocycloalkyl group;

an optionally cationic 5- or 6-membered heteroaryl group, preferentially imidazolium, optionally substituted with a ($C_1$-$C_4$)alkyl group, preferentially methyl;

an amino group substituted with one or two identical or different ($C_1$-$C_5$)alkyl groups, optionally bearing at least:

i) a hydroxyl group;

ii) an amino group optionally substituted with one or two optionally substituted ($C_1$-$C_3$)alkyl groups, said alkyl groups possibly forming, with the nitrogen atom to which they are attached, a saturated or unsaturated, optionally substituted 5- to 7-membered heterocycle, optionally comprising at least one other nitrogen or non-nitrogen heteroatom;

iii) a quaternary ammonium group —N+R'R"R'", M− for which R', R" and R'", which may be identical or different, represent a hydrogen atom or a ($C_1$-$C_4$)alkyl group and M− represents an anionic counterion;

iv) an optionally cationic 5- or 6-membered heteroaryl group, preferentially imidazolium, optionally substituted with a ($C_1$-$C_4$)alkyl group, preferentially methyl;

v) an acylamino (—N(R)—C(O)—R') group wherein R represents a hydrogen atom or a (hydroxy)($C_1$-$C_4$)alkyl group and R' represents a ($C_1$-$C_2$)alkyl group;

an acylamino (—N(R)—C(O)—R') group wherein R represents a hydrogen atom or a (hydroxy)($C_1$-$C_4$)alkyl group and R' represents a ($C_1$-$C_2$)alkyl group;

a carbamoyl group ((R)$_2$N—C(O)—) wherein R, which may be identical or different, represent a hydrogen atom or a (hydroxy)($C_1$-$C_4$)alkyl group;

an alkylsulfonylamino (R'—S(O)₂—N(R)—) group wherein R represents a hydrogen atom or a (hydroxy)(C₁-C₄)alkyl group and R' represents a (C₁-C₄)alkyl group or a phenyl group;

an aminosulfonyl ((R)₂N—S(O)₂—) group wherein R, which may be identical or different, represent a hydrogen atom or a (hydroxy)(C₁-C₄)alkyl group;

a carboxylic group in acid form or salified form (preferably salified with an alkali metal or a substituted or unsubstituted ammonium);

a cyano group;

a nitro or nitroso group;

a polyhaloalkyl group, preferentially trifluoromethyl;

an ester group;

the term "cationic heteroaryl group" is intended to mean a heteroaryl group as defined above, which comprises an endocyclic or exocyclic quaternized cationic group;

when the cationic charge is endocyclic, it is included in the electron delocalization via the mesomeric effect, for example it is a pyridinium, imidazolium or indolinium group:

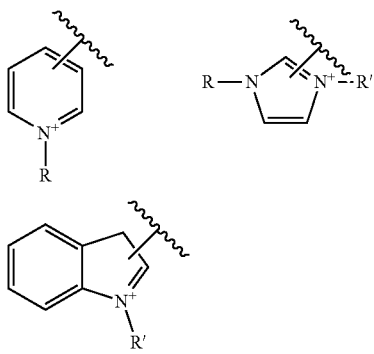

with R and R' being a heteroaryl substituent as defined above and particularly a (hydroxy)(C₁-C₈)alkyl group such as methyl;

when the charge is exocyclic, for example, it is an ammonium substituent R⁺, such as trimethylammonium or phosphonium, which is exterior to the heteroaryl such as pyridinyl, indolyl, imidazolyl or naphthalimidyl in question;

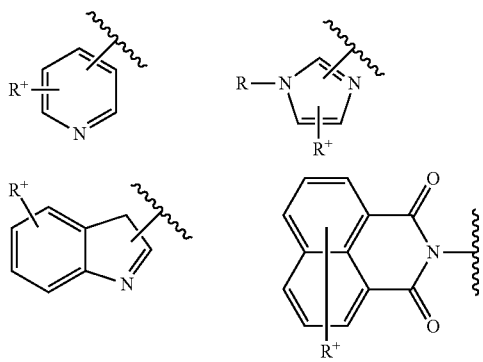

-continued

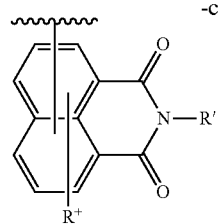

with R a heteroaryl substituent as defined above and R⁺ an ammonium $R_aR_bR_cN^+$—, phosphonium $R_aR_bR_cP^+$— or ammonium $R_aR_bR_cN^+$—(C₁-C₆)alkylamino group with $R_a$, $R_b$ and $R_c$, which may be identical or different, representing a hydrogen atom or a (C₁-C₈)alkyl group such as methyl;

the term "cationic aryl group bearing an exocyclic charge" is intended to mean an aryl ring of which the quaternized cationic group is outside said ring; it is in particular an ammonium substituent R⁺ such as trimethylammonium or phosphonium, which is outside the aryl such as phenyl or naphthyl:

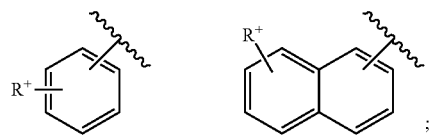

;

the term "(hetero)cyclic group" is intended to mean a heterocyclic group or a carbocyclic group;

the term "heterocyclic group" is intended to mean a 5- to 22-membered monocyclic or fused or non-fused polycyclic group that may contain one or two unsaturations but is nonaromatic, comprising from 1 to 6 heteroatoms chosen from nitrogen, oxygen, sulfur and selenium atoms;

the term "heterocycloalkyl group" is intended to mean a saturated heterocyclic group such as morpholinyl, piperazinyl or piperidinyl;

the term "carbocyclic group" is intended to mean a 5- to 22-membered monocyclic or fused or non-fused polycyclic group that may contain one or two unsaturations but is nonaromatic, such as cyclobutyl, cyclopentyl or cyclohexyl;

the carbocyclic or heterocyclic part of a nonaromatic group may optionally be substituted with at least one group chosen from:

a hydroxyl group;

a (C₁-C₄)alkoxy or hydroxy(C₂-C₄)alkoxy group;

a (C₁-C₄)alkyl group;

an alkylcarbonylamino (R—C(O)—N(R')—) group wherein R' is a hydrogen atom or a (hydroxy)(C₁-C₄) alkyl group and R is a (C₁-C₂)alkyl group or an amino group optionally substituted with one or two identical or different (hydroxy)(C₁-C₄)alkyl groups, said (hydroxy)(C₁-C₄)alkyl groups possibly forming, with the nitrogen atom to which they are attached, a saturated or unsaturated, optionally substituted 5- to 7-membered heterocycle optionally comprising at least one other nitrogen or non-nitrogen heteroatom;

an alkylcarbonyloxy (R—C(O)—O—) group wherein R is a (C₁-C₄)alkyl group or an amino group optionally substituted with one or two identical or different (hydroxy)(C₁-C₄)alkyl groups, said (hydroxy)(C₁-C₄)alkyl groups possibly forming, with the nitrogen atom to which they are attached, a saturated or unsaturated, optionally substituted 5- to 7-membered heterocycle optionally comprising at least one other nitrogen or non-nitrogen heteroatom;

an alkoxycarbonyl (R-G-C(O)—) group wherein R is a ($C_1$-$C_4$)alkyl group, and G is an oxygen atom or an amino group optionally substituted with a (hydroxy)($C_1$-$C_4$)alkyl group;

a cyclic or heterocyclic group, or a nonaromatic part of an aryl or heteroaryl group, may also be substituted with at least one oxo group;

a hydrocarbon-based chain is unsaturated when it includes one or more double bonds and/or one or more triple bonds.

Unless otherwise indicated, when compounds are mentioned in the present patent application, this also includes the optical isomers thereof, the geometrical isomers thereof, the tautomers thereof, the salts thereof or the solvates thereof, alone or as a mixture.

The expressions "at least one" and "one or more" are synonymous and may be used interchangeably.

Dyeing Process

According to a first aspect, a subject of the present invention is a process for dyeing keratin fibers as defined above.

The applicant has found, surprisingly, that the use of a compound of formula (A) in combination with a direct dye makes it possible to obtain a better color build-up and intense and chromatic colors.

a) Direct Dye(s)

The dyeing process uses a) one or more direct dyes. The direct dyes are preferably anionic or neutral.

The direct dyes a) may be neutral, cationic or anionic direct dyes chosen from: acridines; acridones; anthranthrones; anthrapyrimidines; anthraquinones; azines; (poly)azos or azos, hydrazono or hydrazones, in particular arylhydrazones; azomethines; benzanthrones; benzimidazoles; benzimidazolones; benzindoles; benzoxazoles; benzopyrans; benzothiazoles; benzoquinones; bis-isoindolines; carboxanilides; coumarins; cyanines, such as (di)azacarbocyanines, (di)azahemicyanines, hemicyanines or tetraazacarbocyanines; (di)azines; bis-azines; (di)oxazines; (di)thiazines; (di)phenylamines; (di)phenylmethanes; (di)ketopyrrolopyrroles; flavonoids, such as flavanthrones and flavones; fluorindines; formazans; indamines; indanthrones; indigoids, thioindigoids and pseudoindigoids; indophenols; indoanilines; isoindolines; isoindolinones; isoviolanthrones; lactones; (poly)methines, such as dimethines of stilbene or styryl types; naphthalimides; naphthanilides; naphtholactams; naphthoquinones; nitro, notably nitro(hetero)aromatics; oxadiazoles; oxazines; perilones; perinones; perylenes; phenazines; phenoxazines; phenothiazines; phthalocyanines; polyenes/carotenoids; porphyrins; pyranthrones; pyrazolanthrones; pyrazolones; pyrimidinoanthrones; pyronines; quinacridones; quinolines; quinophthalones; squaranes; tetrazolines; thiazines; thiopyronines; triarylmethanes or xanthenes and natural direct dyes. Preferably, the direct dyes a) are chosen from anthraquinones, (poly)azos, azomethines and stilbenes, more preferably from anthraquinones.

The direct dyes a) can be chosen in particular from neutral, cationic or anionic nitrobenzene direct dyes, neutral, cationic or anionic azo direct dyes, neutral, cationic or anionic tetraazapentamethine dyes, cationic or anionic quinone dyes and in particular neutral, cationic or anionic anthraquinone dyes, neutral, cationic or anionic azine direct dyes, neutral, cationic or anionic triarylmethane direct dyes, neutral, cationic or anionic azomethine direct dyes and natural direct dyes. Preferably, the direct dyes are chosen from neutral or anionic anthraquinone dyes and stilbenes.

By way of neutral, anionic or cationic direct dyes that can be used in the present invention, mention may be made of the following dyes: acridines; acridones; anthranthrones; anthrapyrimidines; anthraquinones; azines; (poly)azos, hydrazono or hydrazones, in particular arylhydrazones; azomethines; benzanthrones; benzimidazoles; benzimidazolones; benzindoles; benzoxazoles; benzopyrans; benzothiazoles; benzoquinones; bisazines; bis-isoindolines; carboxanilides; coumarins; cyanines, such as azacarbocyanines, diazacarbocyanines, diazahemicyanines, hemicyanines or tetraazacarbocyanines; diazines; diketopyrrolopyrroles; dioxazines; diphenylamines; diphenylmethanes; dithiazines; flavonoids, such as flavanthrones and flavones; fluorindines; formazans; indamines; indanthrones; indigoids and pseudoindigoids; indophenols; indoanilines; isoindolines; isoindolinones; isoviolanthrones; lactones; (poly)methines, such as dimethines of stilbene or styryl types; naphthalimides; naphthanilides; naphtholactams; naphthoquinones; nitro, notably nitro(hetero)aromatics; oxadiazoles; oxazines; perilones; perinones; perylenes; phenazines; phenoxazine; phenothiazines; phthalocyanine; polyenes/carotenoids; porphyrins; pyranthrones; pyrazolanthrones; pyrazolones; pyrimidinoanthrones; pyronines; quinacridones; quinolines; quinophthalones; squaranes; tetrazoles; thiazines; thioindigo; thiopyronines; triarylmethanes or xanthenes.

Neutral Direct Dyes

The direct dyes a) may be neutral direct dyes, preferably chosen from the hydrazono dyes of formulae (IIIa) and (III'a), the azo and styryl dyes (IVa), the diazo and distyryl dyes (IV'a) and (IV''a), the anthraquinone dyes (Va) and the azomethine dyes (VIa) and (VI'a) below, and mixtures thereof:

(IIIa)
Ar''-C($R^a$)=N-N($R^b$)-Ar

(III'a)
Ar''-N($R^a$)-N=C($R^b$)-Ar

(IVa)
Ar-T=T'-Ar''

(IV'a)
Ar''-T=T'-Ar'-T'=T-Ar

(IV''a)
Ar-T=T'-L-T'=T-Ar

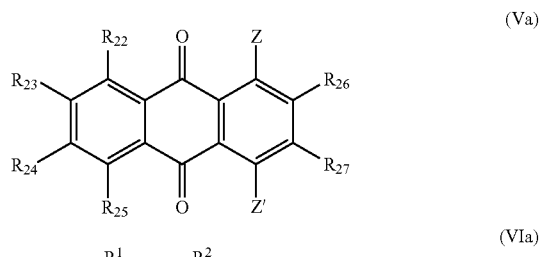

(Va)

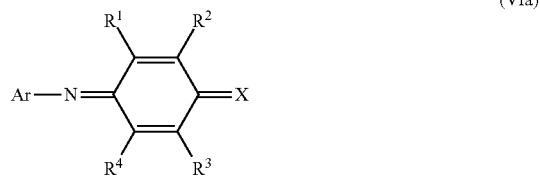

(VIa)

-continued

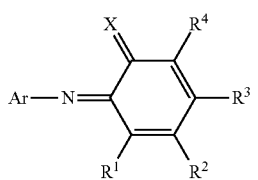
(VI'a)

formulae (IIIa), (III'a), (IVa), (IV'a), (IV''a), (Va), (VIa) and (VI'a) wherein:

Ar represents an aryl group, such as phenyl or naphthyl, substituted with at least one electron-donating group such as i) optionally substituted $(C_1-C_8)$alkyl, ii) optionally substituted $(C_1-C_8)$alkoxy, iii) $(di)(C_1-C_8)$(alkyl)amino optionally substituted on the alkyl group(s) with a hydroxyl group, iv) aryl$(C_1-C_8)$alkylamino, v) optionally substituted N—$(C_1-C_8)$alkyl-N-aryl$(C_1-C_8)$alkylamino or Ar represents a julolidine group;

Ar' represents an optionally substituted divalent (hetero)arylene group such as phenylene, particularly para-phenylene, or naphthalene, which is optionally substituted, preferably with one or more $(C_1-C_8)$alkyl, hydroxyl or $(C_1-C_8)$alkoxy group(s);

Ar'' represents a (hetero)aryl group, which is optionally substituted, preferably with at least i) an electron-withdrawing group such as nitro, nitroso, —C(X)—X'—R' or ii) a $(di)(C_1-C_6)$(alkyl)amino group, iii) hydroxyl, iv) $(C_1-C_6)$alkoxy; (hetero)aryl is particularly chosen from imidazolyl, triazolyl, indolyl or pyridyl or phenyl optionally substituted with at least one group chosen from nitro, nitroso and amino, preferably substituted in the position para to the phenyl group;

X, X' and X'', which may be identical or different, represent an oxygen or sulfur atom, or a group NR'', preferably an oxygen atom;

$R^1$, $R^2$, $R^3$ and $R^4$, which may be identical or different, represent a hydrogen or halogen atom, or a group chosen from hydroxyl, thiol, $(C_1-C_4)$alkyl, $(C_1-C_4)$alkoxy, $(di)(C_1-C_4)$(alkyl)amino, nitro and nitroso;

R' and R'' represent a $(C_1-C_4)$alkyl group;

$R^a$ and $R^b$, which may be identical or different, represent a hydrogen atom or a $(C_1-C_8)$alkyl group, which is optionally substituted, preferably with a hydroxyl group; or, as a variant, the substituent $R^a$ with a substituent of Ar'' and/or $R^b$ with a substituent of Ar and/or $R^a$ with $R^b$ form, together with the atoms that bear them, a (hetero)cycloalkyl; in particular, $R^a$ and $R^b$ represent a hydrogen atom or a $(C_1-C_4)$alkyl group, which is optionally substituted with a hydroxyl group;

T and T', which may be identical or different, represent a group C($R^a$) or N, preferably N; and L represents a divalent group -ALK-, —C(X)-ALK-, -ALK-C(X)— or —C(X)-ALK-C(X')— with ALK representing a linear or branched $(C_1-C_6)$alkylene group, such as methylene, and X and X' as defined above;

$R_{22}$, $R_{23}$, $R_{24}$, $R_{25}$, $R_{26}$ and $R_{27}$, which may be identical or different, represent a hydrogen or halogen atom, or a group chosen from:
$(C_1-C_6)$alkyl;
hydroxyl, mercapto;
$(C_1-C_6)$alkoxy, $(C_1-C_6)$alkylthio;
aryloxy or arylthio;
aryl$(C_1-C_5)$(alkyl)amino;

$(di)(C_1-C_6)$(alkyl)amino;
$(di)(hydroxy(C_1-C_6)alkyl)$amino;

Z' represents a hydrogen atom or a group $NR_{28}R_{29}$ with $R_{28}$ and $R_{29}$, which may be identical or different, representing a hydrogen atom or a group chosen from:
$(C_1-C_6)$alkyl;
polyhydroxy$(C_1-C_6)$alkyl such as hydroxyethyl;
aryl optionally substituted with one or more group(s), particularly i) $(C_1-C_6)$alkyl; iii) $R^o$—C(X)—X'—, $R^o$—X'—C(X)—, $R^o$—X'—C(X)—X''— with $R^o$ representing a $(C_1-C_6)$alkyl group and X, X' and X'' as defined above; iv) a sulfonate;
cycloalkyl; notably cyclohexyl;

Z represents a group chosen from hydroxyl and $NR'_{28}R'_{29}$ with $R'_{28}$ and $R'_{29}$, which may be identical or different, representing the same atoms or groups as $R_{28}$ and $R_{29}$ as defined above;

The direct dyes a) of formula (IV''a) are preferably of formula (IV'''a)

(IV'''a)

[Structure with $R_1O$—, $R_2$, ALK, $R_3$, $R_4$, $OR_3$ and X groups]

formula (IV'''a) wherein:

$R^1$ and $R^3$, which may be identical or different, preferably identical, represent a hydrogen atom, a $(C_1-C_4)$alkyl group such as methyl or a sugar such as glucosyl, preferably a hydrogen atom;

$R^2$ and $R^4$, which may be identical or different, preferably identical, represent a hydrogen atom, a $(C_1-C_4)$alkyl or $(C_1-C_4)$alkoxy group or an —O-sugar group such as —O-glucosyl, preferably $(C_1-C_4)$alkoxy; such as methoxy;

X, which may be identical or different, preferably identical, represents an oxygen or sulfur atom or N—R with R representing a hydrogen atom or a group, preferably an oxygen atom;

ALK represents a $(C_1-C_4)$alkylene group such as methylene or ethylene, preferably methylene.

The direct dyes of formula (IV''a) may be derived from curcumin, demethoxycurcumin and bis-demethoxycurcumin.

Preferably, the direct dyes a) are chosen from the direct dyes of formulae (IV''a) and (IV'''a) and mixtures thereof as defined above.

According to one particularly preferred embodiment, the direct dyes a) are neutral direct dyes chosen from the following compounds (A) to (G) and mixtures thereof:

(A)
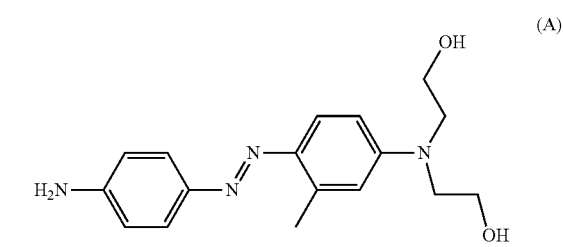

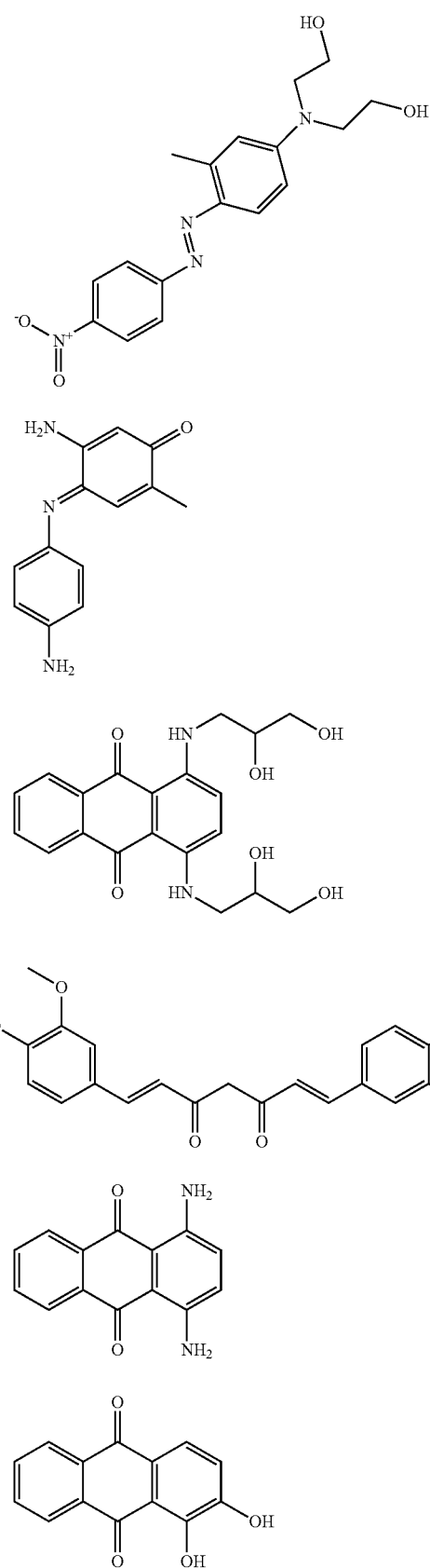

preferably from the compounds (E), (F) and (G) and mixtures thereof, more preferentially from the compounds (E) and (G) and mixtures thereof.

Cationic Direct Dyes

The direct dyes a) can be chosen from dyes which are cationic and direct or commonly referred to as "basic dyes" on account of their affinity for acidic substances.

As cationic azo dyes that can be used in the present invention, mention may be made particularly of the cationic dyes described in the Kirk-Othmer Encyclopedia of Chemical Technology, "Dyes, Azo", J. Wiley & Sons, updated on Apr. 19, 2010.

Mention may also be made of the cationic azo dyes described in patent applications WO 95/15144, WO 95/01772 and EP 714 954.

Mention may also be made of the cationic azo dyes described in the Color Index International 3rd edition, in particular of the following compounds: Basic Red 22; Basic Red 76; Basic Yellow 57; Basic Brown 16; Basic Brown 17.

Among the cationic quinone dyes, those mentioned in the Color Index International, 3rd edition, are suitable and, among these, mention may be made, inter alia, of the following dyes: Basic Blue 22; Basic Blue 99.

Among the azine dyes that are suitable, mention may be made of those listed in the Color Index International, 3rd edition, and for example the following dyes: Basic Blue 17, Basic Red 2.

Among the cationic triarylmethane dyes that can be used according to the invention, mention may be made, in addition to those listed in the Color Index International, 3rd edition, of the following dyes: Basic Green 1, Basic Violet 3, Basic Violet 14, Basic Blue 7, Basic Blue 26.

Mention may also be made of the direct dyes described in U.S. Pat. No. 5,888,252, EP 1 133 975, WO 03/029 359, EP 860 636, WO 95/01772, WO 95/15144 and EP 714 954.

Mention may also be made of those listed in the encyclopedia "The Chemistry of Synthetic Dyes" by K. Venkataraman, 1952, Academic Press, vol. 1 to 7, in the "Kirk-Othmer Encyclopedia of Chemical Technology", in the chapter "Dyes and Dye Intermediates", 1993, Wiley and Sons, and in various chapters of "Ullmann's Encyclopedia of Industrial Chemistry", 7th edition, Wiley and Sons.

Preferably, the cationic direct dyes are chosen from those resulting from dyes of azo and hydrazono type.

The cationic direct dyes may be cationic azo dyes, as described in EP 850 636, FR 2 788 433, EP 920 856, WO 99/48465, FR 2 757 385, EP 850 637, EP 918 053, WO 97/44004, FR 2 570 946, FR 2 285 851, DE 2 538 363, FR 2 189 006, FR 1 560 664, FR 1 540 423, FR 1 567 219, FR 1 516 943, FR 1 221 122, DE 4220388, DE 4 137 005, WO 01/66646, U.S. Pat. No. 5,708,151, WO 95/01772, WO 515 144, GB 1 195 386, U.S. Pat. Nos. 3,524,842, 5,879,413, EP 1 062 940, EP 1 133 976, GB 738 585, DE 2 527 638, FR 2 275 462, GB 1974-27645, Acta Histochem. (1978), 61(1), 48-52; Tsitologiya (1968), 10(3), 403-5; Zh. Obshch. Khim. (1970), 40(1), 195-202; Ann. Chim. (Rome) (1975), 65(5-6), 305-14; Journal of the Chinese Chemical Society (Taipei) (1998), 45(1), 209-211; Rev. Roum. Chim. (1988), 33(4), 377-83; Text. Res. J. (1984), 54(2), 105-7; Chim. Ind. (Milan) (1974), 56(9), 600-3; Khim. Tekhnol. (1979), 22(5), 548-53; Ger. Monatsh. Chem. (1975), 106(3), 643-8; MRL Bull. Res. Dev. (1992), 6(2), 21-7; Lihua Jianyan, Huaxue Fence (1993), 29(4), 233-4; Dyes Pigm. (1992), 19(1), 69-79; Dyes Pigm. (1989), 11(3), 163-72.

Preferably, the cationic direct dyes comprise a quaternary ammonium group; more preferentially, the cationic charge is endocyclic. These cationic groups are, for example, a cationic group:
- bearing a (di/tri)($C_1$-$C_8$)alkylammonium exocyclic charge, or
- bearing an endocyclic charge, such as comprising a cationic heteroaryl group chosen from: acridinium, benzimidazolium, benzobistriazolium, benzopyrazolium, benzopyridazinium, benzoquinolium, benzothiazolium, benzotriazolium, benzoxazolium, bipyridinium, bis-tetrazolium, dihydrothiazolium, imidazopyridinium, imidazolium, indolium, isoquinolium, naphthoimidazolium, naphthoxazolium, naphthopyrazolium, oxadiazolium, oxazolium, oxazolopyridinium, oxonium, *phenazinium*, phenoxazolium, pyrazinium, pyrazolium, pyrazoyltriazolium, pyridinium, pyridinoimidazolium, pyrrolium, pyrylium, quinolium, tetrazolium, thiadiazolium, thiazolium, thiazolopyridinium, thiazoylimidazolium, thiopyrylium, triazolium or xanthylium.

Mention may be made of the hydrazono cationic direct dyes of formulae (IIb) and (IIIb) and the azo dyes of formulae (IVb) and (Vb) below:

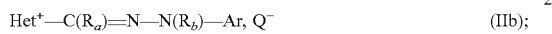  (IIb);

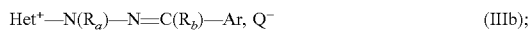  (IIIb);

  (IVb);

  (Vb);

formulae (IIb) to (Vb) wherein:
Het$^+$ represents a cationic heteroaryl group, preferentially bearing an endocyclic cationic charge, such as imidazolium, indolium or pyridinium, which is optionally substituted, preferentially with at least one ($C_1$-$C_8$) alkyl group such as methyl;

Ar$^+$ represents an aryl group, such as phenyl or naphthyl, bearing an exocyclic cationic charge, preferentially ammonium, particularly tri($C_1$-$C_8$)alkylammonium, such as trimethylammonium:

Ar represents an aryl group, in particular phenyl, which is optionally substituted, preferentially with one or more electron-donating groups such as i) optionally substituted ($C_1$-$C_8$)alkyl, ii) optionally substituted ($C_1$-$C_8$) alkoxy, iii) (di)($C_1$-$C_8$)(alkyl)amino optionally substituted on the alkyl group(s) with a hydroxyl group, iv) aryl($C_1$-$C_8$)alkylamino, v) optionally substituted N—($C_1$-$C_8$)alkyl-N-aryl($C_1$-$C_8$)alkylamino or alternatively Ar represents a julolidine group;

Ar'' represents an optionally substituted (hetero)aryl group, such as phenyl or pyrazolyl, which are optionally substituted, preferentially with one or more ($C_1$-$C_8$)alkyl, hydroxyl, (di)($C_1$-$C_8$)(alkyl)amino, ($C_1$-$C_8$) alkoxy or phenyl groups;

$R_a$ and $R_b$, which may be identical or different, represent a hydrogen atom or a ($C_1$-$C_8$)alkyl group, which is optionally substituted, preferentially with a hydroxyl group;

or else the substituent $R_a$ with a substituent of Het$^+$ and/or $R_b$ with a substituent of Ar and/or $R_a$ with $R_b$ form, together with the atoms that bear them, a (hetero) cycloalkyl; in particular, $R_a$ and $R_b$ represent a hydrogen atom or a ($C_1$-$C_4$)alkyl group optionally substituted with a hydroxyl group;

Q$^-$ represents an anionic counterion such as a halide, an alkyl sulfate or an alkylsulfonate.

In particular, mention may be made of the azo and hydrazono direct dyes bearing an endocyclic cationic charge of formulae (IIb) to (Vb) as defined above. More particularly, mention may be made of the cationic direct dyes of formulae (IIb) to (Vb) bearing an endocyclic cationic charge described in patent applications WO 95/15144, WO 95/01772 and EP 714 954.

Preferably, mention may be made of the following direct dyes:

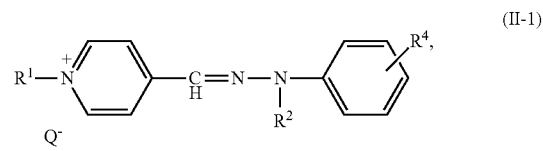 (II-1)

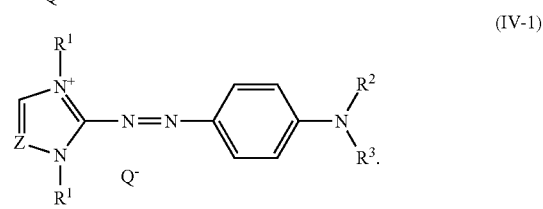 (IV-1)

formulae (II-1) and (IV-1) wherein:

$R^1$ represents a ($C_1$-$C_4$)alkyl group such as methyl;

$R^2$ and $R^3$, which may be identical or different, represent a hydrogen atom or a ($C_1$-$C_4$)alkyl group, such as methyl;

$R^4$ represents a hydrogen atom or an electron-donating group such as optionally substituted ($C_1$-$C_8$)alkyl, optionally substituted ($C_1$-$C_8$)alkoxy, or (di)($C_1$-$C_8$) (alkyl)amino optionally substituted on the alkyl group(s) with a hydroxyl group; particularly, $R^4$ is a hydrogen atom, Z represents a CH group or a nitrogen atom, preferentially CH, Q$^-$ is an anionic counterion as defined above, in particular a halide, such as chloride, or an alkyl sulfate, such as methyl sulfate or mesityl.

In particular, the dyes of formulae (II-1) and (IV-1) are chosen from Basic Red 51, Basic Yellow 87 and Basic Orange 31 or derivatives thereof:

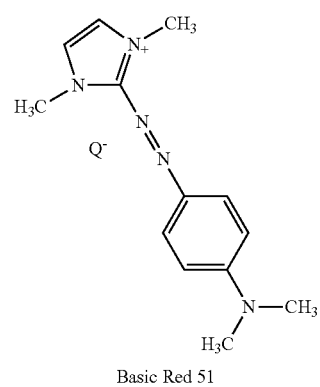

Basic Red 51

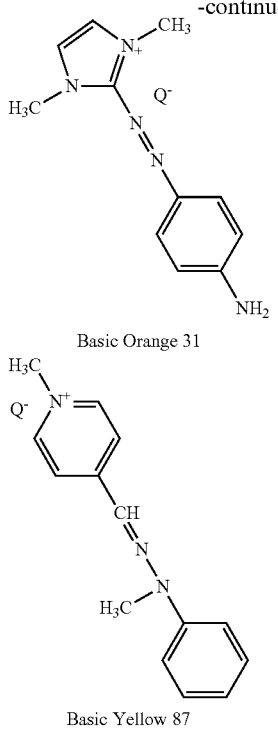

Basic Orange 31

Basic Yellow 87 with Q⁻ being an anionic counterion as defined above, in particular a halide, such as chloride, or an alkyl sulfate, such as methyl sulfate or mesityl.

Fluorescent Dyes

The direct dyes a) can be chosen from fluorescent direct dyes.

By way of example of fluorescent dyes that may be used in the present invention, mention may be made of neutral, anionic or cationic dyes chosen from the following dyes: acridines, acridones, benzanthrones, benzimidazoles, benzimidazolones, benzindoles, benzoxazoles, benzopyrans, benzothiazoles, coumarins, difluoro{2-[(2H-pyrrol-2-ylidene-kN)methyl]-1H-pyrrolato-kN}borons (BODIPY®), diketopyrrolopyrroles, fluorindines, (poly)methines (in particular cyanines and styryls/hemicyanines), naphthalimides, naphthanilides, naphthylamines (such as dansyls), oxadiazoles, oxazines, perilones, perinones, perylenes, polyenes/carotenoids, squaranes, stilbenes, xanthenes.

Mention may also be made of the fluorescent dyes described in EP 1 133 975, WO 03/029 359, EP 860 636, WO 95/01772, WO 95/15144 and EP 714 954 and those listed in the encyclopedia "The Chemistry of Synthetic Dyes" by K. Venkataraman, 1952, Academic Press, vol. 1 to 7, in the "Kirk-Othmer Encyclopedia of Chemical Technology", in the chapter "Dyes and Dye Intermediates", 1993, Wiley and Sons, and in various chapters of "Ullmann's Encyclopedia of Industrial Chemistry", 7th edition, Wiley and Sons, and in the handbook—"A Guide to Fluorescent Probes and Labeling Technologies", 10th Ed., Molecular Probes/Invitrogen—Oregon 2005, circulated on the Internet or in the preceding printed editions.

According to a preferred variant, the fluorescent dye(s) are cationic polymethines and comprise at least one quaternary ammonium group, such as those of formula (Vb) below:

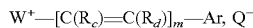

formula (Vb) wherein:

W⁺ represents a cationic heterocyclic or heteroaryl group, particularly comprising a quaternary ammonium optionally substituted with one or more $(C_1-C_8)$alkyl groups, optionally substituted notably with one or more hydroxyl groups;

Ar representing an aryl group such as phenyl or naphthyl, optionally substituted preferentially with i) one or more halogen atoms such as chlorine or fluorine; ii) one or more $(C_1-C_8)$alkyl, preferably $(C_1-C_4)$ alkyl groups such as methyl; iii) one or more hydroxyl groups; iv) one or more $(C_1-C_8)$alkoxy groups such as methoxy; v) one or more hydroxy$(C_1-C_8)$alkyl groups such as hydroxyethyl, vi) one or more amino or (di)$(C_1-C_8)$ alkylamino groups, preferably with the $C_1-C_4$ alkyl part optionally substituted with one or more hydroxyl groups, such as (di)hydroxyethylamino, vii) one or more acylamino groups; viii) one or more heterocycloalkyl groups such as piperazinyl, piperidinyl or 5- or 6-membered heteroaryl such as pyrrolidinyl, pyridinyl and imidazolinyl;

m' represents an integer ranging from 1 to 4, preferably m' is equal to 1 or 2; more preferentially m'=1;

$R_c$ and $R_d$, which may be identical or different, represent a hydrogen atom or an optionally substituted $(C_1-C_8)$ alkyl group, preferentially an optionally substituted $(C_1-C_4)$alkyl group, or else $R_c$ contiguous with W⁺ and/or $R_d$ contiguous with Ar form, with the atoms that bear them, a (hetero)cycloalkyl; particularly, $R_c$ is contiguous with W⁺ and they form a (hetero)cycloalkyl such as cyclohexyl;

Q⁻ is an anionic counterion as defined above.

Anionic Dyes

The direct dyes a) can be chosen from anionic direct dyes or dyes commonly referred to as "acidic" direct dyes on account of their affinity for alkaline substances.

The term "anionic direct dye" is intended to mean any direct dye including in its structure at least one $CO_2R$ or $SO_3R$ substituent with R denoting a hydrogen atom or a cation originating from a metal or an amine, or an ammonium ion. The anionic dyes can be chosen from acid nitro direct dyes, acid azo dyes, acid azine dyes, acid triarylmethane dyes, acid indoamine dyes, acid anthraquinone dyes, indigoids and acid natural dyes.

Preferably, the anionic direct dyes are acidic anthraquinones.

The direct dyes a) can be anionic direct dyes preferably chosen from the dyes of formulae (III), (III'), (IV), (IV'), (V), (V'), (VI), (VI'), (VII), (VIII), (IX) and (X) below, and mixtures thereof:

a) The Diaryl Anionic Azo Dyes of Formula (III) or (III'):

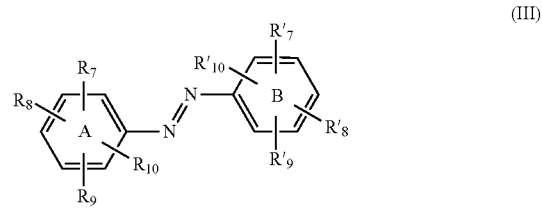

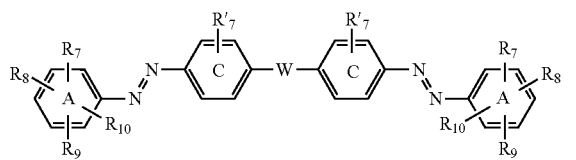

formulae (III) and (III') wherein:

$R_7$, $R_8$, $R_9$, $R_{10}$, $R'_7$, $R'_8$, $R'_9$ and $R'_{10}$, which may be identical or different, represent a hydrogen atom or a group chosen from:

($C_1$-$C_6$)alkyl;

($C_1$-$C_6$)alkoxy, ($C_1$-$C_6$)alkylthio;

hydroxyl, mercapto;

nitro, nitroso;

$R^o$—C(X)—X'—, $R^o$—X'—C(X)—, $R^o$—X'—C(X)—X"— with $R^o$ representing a hydrogen atom or a ($C_1$-$C_6$)alkyl or aryl group such as phenyl; X, X' and X", which may be identical or different, representing an oxygen or sulfur atom, or NR with R representing a hydrogen atom or a ($C_1$-$C_6$)alkyl group;

$(O)_2S(O^-)$—, $M^+$ with $M^+$ representing a hydrogen atom or a cationic counterion;

$(O)CO^-$—, $M^+$ with $M^+$ as defined above;

R'''—$S(O)_2$—, with R''' representing a hydrogen atom, an alkyl group, or an aryl, (di)($C_1$-$C_6$)(alkyl)amino, or aryl($C_1$-$C_6$)(alkyl)amino group; preferentially a phenylamino or phenyl group;

R'''—$S(O)_2$—X'— with R''' representing a ($C_1$-$C_6$)alkyl group or an aryl group which is optionally substituted, X' as defined above;

(di)($C_1$-$C_6$)(alkyl)amino;

aryl($C_1$-$C_6$)(alkyl)amino optionally substituted with one or more group(s) chosen from i) nitro; ii) nitroso; iii) $(O)_2S(O^-)$—, $M^+$ and iv) ($C_1$-$C_6$)alkoxy with $M^+$ as defined above;

optionally substituted heteroaryl; preferentially a benzothiazolyl group;

cycloalkyl; notably cyclohexyl;

Ar—N=N— with Ar representing an optionally substituted aryl group; preferentially a phenyl optionally substituted with one or more alkyl, $(O)_2S(O^-)$—, $M^+$ or phenylamino group(s);

or else two contiguous groups $R_7$ with $R_8$ or $R_8$ with $R_9$ or $R_9$ with $R_{10}$ together form a fused benzo group A'; and $R'_7$ with $R'_8$ or $R'_8$ with $R'_9$ or $R'_9$ with $R'_{10}$ together form a fused benzo group B'; with A' and B' optionally substituted with one or more group(s) chosen from i) nitro; ii) nitroso; iii) $(O)_2S(O^-)$—, $M^+$; iv) hydroxyl; v) mercapto; vi) (di)(alkyl)amino; vii) $R^o$—C(X)—X'—; viii) $R^o$—X'—C(X)—; ix) $R^o$—X'—C(X)—X"—; x) Ar—N=N— and xi) optionally substituted aryl(alkyl)amino; with $M^+$, $R^o$, X, X', X" and Ar as defined above;

W represents a sigma bond, an oxygen or sulfur atom, or a divalent group i) —NR— with R as defined above, or ii) methylene —C($R_a$)($R_b$)— with $R_a$ and $R_b$, which may be identical or different, representing a hydrogen atom or an aryl group, or alternatively $R_a$ and $R_b$ together form, with the carbon atom that bears them, a spiro cycloalkyl; preferentially, W represents a sulfur atom or $R_a$ and $R_b$ together form a cyclohexyl;

it being understood that formulae (III) and (III') comprise, on one of the rings A, A', B, B' or C:

at least one group $(O)_2S(O^-)$—, $M'^+$ with $M'^+$ representing a cationic counterion; or at least one group $(O)CO^-$—, $M'^+$ with $M'^+$ representing a cationic counterion;

preferably at least one sodium sulfonate group.

As examples of dyes of formula (III), mention may be made of: Acid Red 1, Acid Red 4, Acid Red 13, Acid Red 14, Acid Red 18, Acid Red 27, Acid Red 28, Acid Red 32, Acid Red 33, Acid Red 35, Acid Red 37, Acid Red 40, Acid Red 41, Acid Red 42, Acid Red 44, Pigment red 57, Acid Red 68, Acid Red 73, Acid Red 135, Acid Red 138, Acid Red 184, Food Red 1, Food Red 13, Acid Orange 6, Acid Orange 7, Acid Orange 10, Acid Orange 19, Acid Orange 20, Acid Orange 24, Yellow 6, Acid Yellow 9, Acid Yellow 36, Acid Yellow 199, Food Yellow 3, Acid Violet 7, Acid Violet 14, Acid Blue 113, Acid Blue 117, Acid Black 1, Acid Brown 4, Acid Brown 20, Acid Black 26, Acid Black 52, Food Black 1, Food Black 2, Food Yellow 3 or Sunset Yellow;

and as examples of dyes of formula (III'), mention may be made of: Acid Red 111, Acid Red 134, Acid Yellow 38;

b) The Pyrazolone Anionic Azo Dyes of Formula (IV) or (IV'):

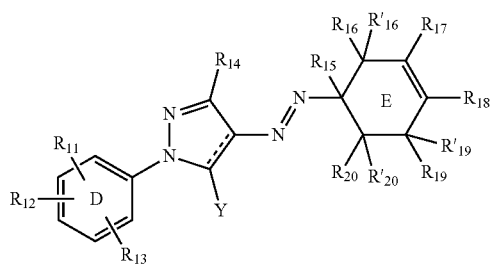

-continued

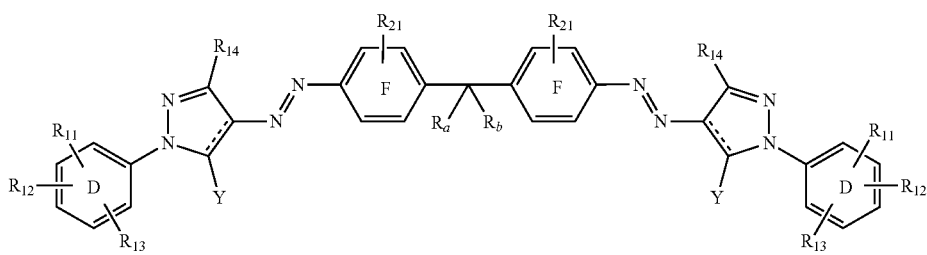
(IV')

formulae (IV) and (IV') wherein:
$R_{11}$, $R_{12}$ and $R_{13}$, which may be identical or different, represent a hydrogen or halogen atom, a $(C_1-C_6)$alkyl group or $—(O)_2S(O^-)$, $M^+$ with $M^+$ as defined above;
$R_{14}$ represents a hydrogen atom, a $(C_1-C_6)$alkyl group or a $—C(O)O—$, $M^+$ group with $M^+$ as defined above;
$R_{15}$ represents a hydrogen atom;
$R_{16}$ represents an oxo group, in which case $R'_{16}$ is absent, or else $R_{15}$ with $R_{16}$ together form a double bond:
$R_{17}$ and $R_{18}$, which may be identical or different, represent a hydrogen atom or a group chosen from:
$(O)_2S(O^-)—$, $M^+$ with $M^+$ as defined above;
$Ar—O—S(O)_2—$ with Ar representing an optionally substituted aryl group; preferentially a phenyl optionally substituted with one or more alkyl group(s);
$R_{19}$ and $R_{20}$ together form either a double bond, or a benzo group D', which is optionally substituted;
$R'_{16}$, $R'_{19}$ and $R'_{20}$, which may be identical or different, represent a hydrogen atom or a $(C_1-C_6)$alkyl group, or a hydroxyl group;
$R_{21}$ represents a hydrogen atom or a $(C_1-C_6)$alkyl or $(C_1-C_6)$alkoxy group;
$R_a$ and $R_b$, which may be identical or different, are as defined above; preferentially, $R_a$ represents a hydrogen atom and $R_b$ represents an aryl group such as phenyl;
Y represents either a hydroxyl group or an oxo group;
--- represents a single bond when Y is an oxo group; and represents a double bond when Y represents a hydroxyl group;
it being understood that formulae (IV) and (IV') comprise, on one of the rings D or E:
at least one group $(O)_2S(O^-)—$, $M'^+$ with $M'^+$ representing a cationic counterion; or
at least one group $(O)CO^-—$, $M'^+$ with $M'^+$ representing a cationic counterion;
preferably at least one sodium sulfonate group.

As examples of dyes of formula (IV), mention may be made of: Acid Red 195, Acid Yellow 23, Acid Yellow 27, Acid Yellow 76, and as examples of dyes of formula (IV'), mention may be made of: Acid Yellow 17;
c) The Anthraquinone Dyes of Formula (V) or (V'):

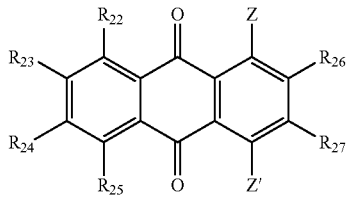
(V)

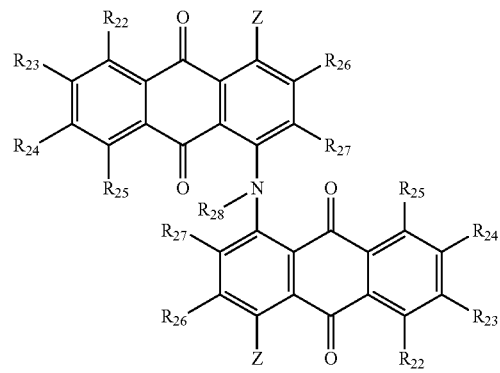
(V')

formulae (V) and (V') wherein:
$R_{22}$, $R_{23}$, $R_{24}$, $R_{25}$, $R_{26}$ and $R_{27}$, which may be identical or different, represent a hydrogen or halogen atom, or a group chosen from:
$(C_1-C_6)$alkyl;
hydroxyl, mercapto;
$(C_1-C_6)$alkoxy, $(C_1-C_6)$alkylthio;
optionally substituted aryloxy or arylthio, preferentially substituted with one or more group(s) chosen from alkyl and $(O)_2S(O^-)—$, $M^+$ with $M^+$ as defined above;
aryl$(C_1-C_6)$(alkyl)amino optionally substituted with one or more group(s) chosen from alkyl and $(O)_2S(O^-)—$, $M^+$ with $M^+$ as defined above;
(di)$(C_1-C_6)$(alkyl)amino;
(di)(hydroxy$(C_1-C_6)$alkyl)amino;
$(O)_2S(O^-)—$, $M^+$ with $M^+$ as defined above;
Z' represents a hydrogen atom or a group $NR_{28}R_{29}$ with $R_{28}$ and $R_{29}$, which may be identical or different, representing a hydrogen atom or a group chosen from:
$(C_1-C_6)$alkyl;
polyhydroxy$(C_1-C_6)$alkyl such as hydroxyethyl;
aryl optionally substituted with one or more group(s), particularly i) $(C_1-C_6)$alkyl such as methyl, n-dodecyl, n-butyl; ii) $(O)_2S(O^-)—$, $M^+$ with $M^+$ as defined above; iii) $R°—C(X)—X'—$, $R°—X'—C(X)—$, $R°—X'—C(X)—X"—$ with $R°$, X, X' and X" as defined above; preferentially $R°$ represents a $(C_1-C_6)$alkyl group;
cycloalkyl, notably cyclohexyl;
Z represents a group chosen from hydroxyl and $NR'_{28}R'_{29}$ with $R'_{28}$ and $R'_{29}$, which may be identical or different, representing the same atoms or groups as $R_{28}$ and $R_{29}$ as defined above;
it being understood that formulae (V) and (V') comprise:
at least one group $(O)_2S(O^-)—$, $M'^+$ with $M'^+$ representing a cationic counterion; or at least one group (O)CO⁻—, M'⁺ with M'⁺ representing a cationic counterion;
preferably at least one sodium sulfonate group.

As examples of dyes of formula (V), mention may be made of: Acid Blue 25, Acid Blue 43, Acid Blue 62, Acid Blue 78, Acid Blue 129, Acid Blue 138, Acid Blue 140, Acid Blue 251, Acid Green 25, Acid Green 41, Acid Violet 42, Acid Violet 43, Mordant Red 3; EXT violet No. 2;

and as examples of dyes of formula (V'), mention may be made of: Acid Black 48;

d) The Nitro Dyes of Formula (VI) or (VI'):

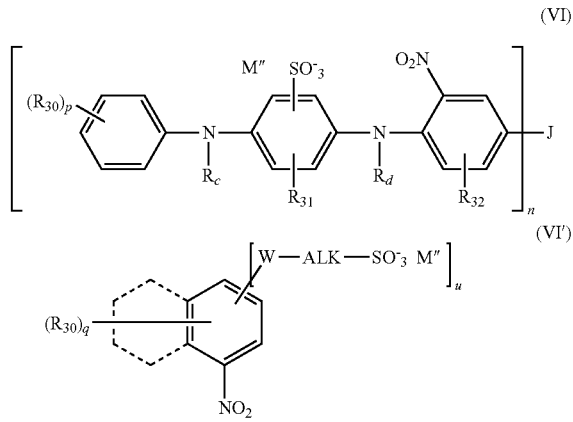

formulae (VI) and (VI') wherein:
$R_{30}$, $R_{31}$ and $R_{32}$, which may be identical or different, represent a hydrogen or halogen atom, or a group chosen from:
($C_1$-$C_6$)alkyl;
($C_1$-$C_6$)alkoxy optionally substituted with one or more hydroxyl group(s) or ($C_1$-$C_6$)alkylthio optionally substituted with one or more hydroxyl group(s);
hydroxyl, mercapto;
nitro, nitroso;
polyhalo($C_1$-$C_6$)alkyl;
$R°$—C(X)—X'—, $R°$—X'—C(X)—, $R°$—X'—C(X)—X"— with $R°$, X, X' and X" as defined above;
$(O)_2S(O^-)$—, $M^+$ with $M^+$ as defined above;
$(O)CO^-$—, $M^+$ with $M^+$ as defined above;
(di)($C_1$-$C_6$)(alkyl)amino;
(di)(hydroxy($C_1$-$C_6$)alkyl)amino;
heterocycloalkyl such as piperidino, piperazino or morpholino;
in particular, $R_{30}$, $R_{31}$ and $R_{32}$ represent a hydrogen atom;
$R_c$ and $R_d$, which may be identical or different, represent a hydrogen atom or a ($C_1$-$C_6$)alkyl group;
W is as defined above; W particularly represents an N(H)— group;
ALK represents a linear or branched divalent $C_1$-$C_6$ alkylene group; in particular, ALK represents a —CH₂—CH₂— group;
n is 1 or 2;
p represents an integer ranging from 1 to 5;
q represents an integer ranging from 1 to 4;
u is 0 or 1;
when n is 1, J represents a nitro or nitroso group; particularly nitro;
when n is 2, J represents an oxygen or sulfur atom, or a divalent group —S(O)ₘ— with m representing an integer 1 or 2; preferentially, J represents an —SO₂— group;
M" represents a hydrogen atom or a cationic counterion;

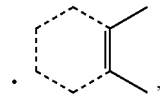

which may be present or absent, represents a benzo group optionally substituted with one or more groups $R_{30}$ as defined above;
it being understood that formulae (VI) and (VI') comprise:
at least one group $(O)_2S(O^-)$—, M'⁺ with M'⁺ representing a cationic counterion; or
at least one group (O)CO⁻—, M'⁺ with M'⁺ representing a cationic counterion;
preferably at least one sodium sulfonate group.

As examples of dyes of formula (VI), mention may be made of: Acid Brown 13 and Acid Orange 3; as examples of dyes of formula (VI'), mention may be made of: Acid Yellow 1, the sodium salt of 2,4-dinitro-1-naphthol-7-sulfonic acid, 2-piperidino-5-nitrobenzenesulfonic acid, 2-(4'-N,N-(2"-hydroxyethyl)amino-2'-nitro)anilineethanesulfonic acid, 4-β-hydroxyethylamino-3-nitrobenzenesulfonic acid; EXT D&C Yellow 7;

e) The Triarylmethane Dyes of Formula (VII):

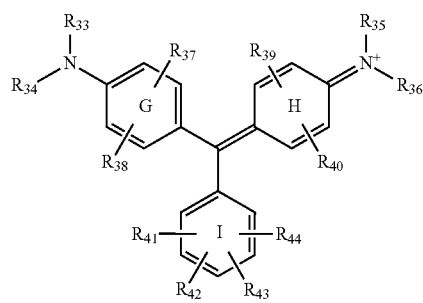

formula (VII) wherein:
$R_{33}$, $R_{34}$, $R_{35}$ and $R_{36}$, which may be identical or different, represent a hydrogen atom or a group chosen from ($C_1$-$C_6$)alkyl, optionally substituted aryl and optionally substituted aryl($C_1$-$C_6$)alkyl; particularly a ($C_1$-$C_6$)alkyl group and benzyl optionally substituted with an $(O)_mS(O^-)$—, $M^+$ group with $M^+$ and m as defined above;
$R_{37}$, $R_{38}$, $R_{39}$, $R_{40}$, $R_{41}$, $R_{42}$, $R_{43}$ and $R_{44}$, which may be identical or different, represent a hydrogen atom or a group chosen from:
($C_1$-$C_6$)alkyl;
($C_1$-$C_6$)alkoxy, ($C_1$-$C_6$)alkylthio;
(di)($C_1$-$C_6$)(alkyl)amino;
hydroxyl, mercapto;
nitro, nitroso;
$R°$—C(X)—X'—, $R°$—X'—C(X)—, $R°$—X'—C(X)—X"— with $R°$ representing a hydrogen atom or an alkyl or aryl group; X, X' and X", which may be identical or different, representing an oxygen or sulfur atom, or NR with R representing a hydrogen atom or a ($C_1$-$C_6$)alkyl group;
$(O)_2S(O^-)$—, $M^+$ with $M^+$ representing a hydrogen atom or a cationic counterion;

(O)CO$^-$—, M$^+$ with M$^+$ as defined above;

or else two contiguous groups R$_{41}$ with R$_{42}$ or R$_{42}$ with R$_{43}$ or R$_{43}$ with R$_{44}$ together form a fused benzo group optionally substituted with one or more group(s) chosen from i) nitro; ii) nitroso; iii) (O)$_2$S(O$^-$)—, M$^+$; iv) hydroxyl; v) mercapto; vi) (di)(C$_1$-C$_6$)(alkyl)amino; vii) R$^o$—C(X)—X'—; viii) R$^o$—X'—C(X)—; ix) R$^o$—X'—C(X)—X"—; with M$^+$, R$^o$, X, X' and X" as defined above;

particularly, R$_{37}$ to R$_{40}$ represent a hydrogen atom, and R$_{41}$ to R$_{44}$, which may be identical or different, represent a hydroxyl group or (O)$_2$S(O$^-$)—, M$^+$ with M$^+$ as defined above; and when R$_{43}$ with R$_{44}$ together form a benzo group, it is preferentially substituted with an (O)$_2$S(O$^-$)— group;

it being understood that at least one of the rings G, H or I comprises:

at least one group (O)$_2$S(O$^-$)—, M'$^+$ with M'$^+$ representing a cationic counterion; or at least one group (O)CO$^-$—, M'$^+$ with M'$^+$ representing a cationic counterion;

preferably at least one sodium sulfonate group.

As examples of dyes of formula (VII), mention may be made of: Acid Blue 1; Acid Blue 3; Acid Blue 7, Acid Blue 9; Acid Violet 49; Acid Green 3; Acid Green 5 and Acid Green 50;

f) The Xanthene-Based Dyes of Formula (VIII):

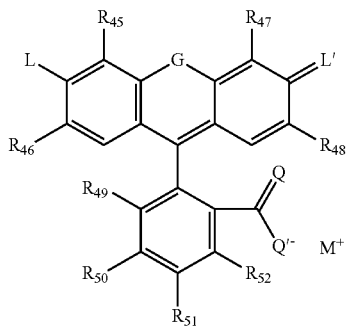

(VIII)

formula (VIII) wherein:

R$_{45}$, R$_{46}$, R$_{47}$ and R$_{48}$, which may be identical or different, represent a hydrogen atom or a halogen atom;

R$_{49}$, R$_{50}$, R$_{51}$ and R$_{52}$, which may be identical or different, represent a hydrogen or halogen atom, or a group chosen from:

(C$_1$-C$_6$)alkyl;

(C$_1$-C$_6$)alkoxy, (C$_1$-C$_6$)alkylthio;

hydroxyl, mercapto;

nitro, nitroso;

(O)$_2$S(O$^-$)—, M$^+$ with M$^+$ representing a hydrogen atom or a cationic counterion;

(O)CO$^-$—, M$^+$ with M$^+$ as defined above;

particularly, R$_{45}$, R$_{46}$, R$_{47}$ and R$_{48}$ represent a hydrogen or halogen atom;

G represents an oxygen or sulfur atom or a group NR$_e$ with R$_e$ as defined above; particularly, G represents an oxygen atom;

L represents an alkoxide O$^-$, M$^+$; a thioalkoxide S$^-$, M$^+$ or a group NR$_f$, with R$_f$ representing a hydrogen atom or a (C$_1$-C$_6$)alkyl group, and M$^+$ as defined above; M$^+$ is particularly sodium or potassium;

L' represents an oxygen or sulfur atom or an ammonium group: N$^+$ R$_f$R$_g$, with R$_f$ and R$_g$, which may be identical or different, representing a hydrogen atom, a (C$_1$-C$_6$) alkyl group or an optionally substituted aryl group; L' represents particularly an oxygen atom or a phenylamino group optionally substituted with one or more alkyl or (O)$_m$S(O$^-$)—, M$^+$ group(s) with m and M$^+$ as defined above;

Q and Q', which may be identical or different, represent an oxygen or sulfur atom; particularly Q and Q' represent an oxygen atom;

M$^+$ is as defined above.

As examples of dyes of formula (VIII), mention may be made of: Acid Yellow 73; Acid Red 51; Acid Red 52; Acid Red 87; Acid Red 92; Acid Red 95; Acid Violet 9;

g) The Indole-Based Dyes of Formula (IX):

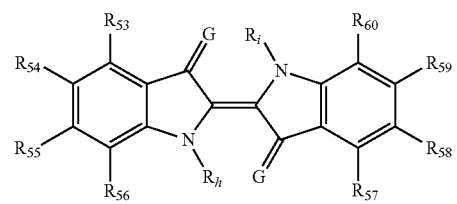

(IX)

formula (IX) wherein:

R$_{53}$, R$_{54}$, R$_{55}$, R$_{56}$, R$_{57}$, R$_{58}$, R$_{59}$ and R$_{60}$, which may be identical or different, represent a hydrogen atom or a group chosen from:

(C$_1$-C$_6$)alkyl;

(C$_1$-C$_6$)alkoxy, (C$_1$-C$_6$)alkylthio;

hydroxyl, mercapto;

nitro, nitroso;

R$^o$—C(X)—X'—, R$^o$—X'—C(X)—, R$^o$—X'—C(X)—X"— with R$^o$ representing a hydrogen atom or an alkyl or aryl group; X, X' and X", which may be identical or different, representing an oxygen or sulfur atom, or NR with R representing a hydrogen atom or a (C$_1$-C$_6$)alkyl group;

(O)$_2$S(O$^-$)—, M$^+$ with M$^+$ representing a hydrogen atom or a cationic counterion;

(O)CO$^-$—, M$^+$ with M$^+$ as defined above;

G represents an oxygen or sulfur atom or a group NR$_e$ with R$_e$ as defined above; particularly, G represents an oxygen atom;

R$_i$ and R$_h$, which may be identical or different, represent a hydrogen atom or a (C$_1$-C$_6$)alkyl group;

it being understood that formula (IX) comprises:

at least one group (O)$_2$S(O$^-$)—, M'$^+$ with M'$^+$ representing a cationic counterion; or at least one group (O)CO$^-$—, M'$^+$ with M'$^+$ representing a cationic counterion;

preferably at least one sodium sulfonate group.

As examples of dyes of formula (IX), mention may be made of: Acid Blue 74;

h) The Quinoline-Based Dyes of Formula (X):

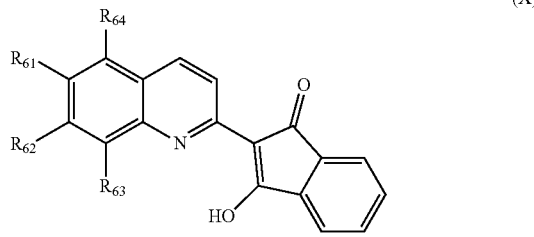

formula (X) wherein:

$R_{61}$ represents a hydrogen or halogen atom or a $(C_1-C_6)$ alkyl group;

$R_{62}$, $R_{63}$ and $R_{64}$, which may be identical or different, represent a hydrogen atom or a group $(O)_2S(O^-)$—, $M^+$ with $M^+$ representing a hydrogen atom or a cationic counterion; or else $R_{61}$ with $R_{62}$, or $R_{61}$ with $R_{64}$, together form a benzo group optionally substituted with one or more groups $(O)_2S(O^-)$—, $M^+$ with $M^+$ representing a hydrogen atom or a cationic counterion;

it being understood that formula (X) comprises at least one group $(O)_2S(O^-)$—, $M'^+$ with $M'^+$ representing a cationic counterion, preferably at least one sodium sulfonate group.

As examples of dyes of formula (X), mention may be made of: Acid Yellow 2, Acid Yellow 3 and Acid Yellow 5.

More particularly, the dyes of formulae (III) to (VIII) that are useful in the invention are chosen from: Acid Red 87 (VIII) (C.I. 45380); Sodium salt of 2,4-dinitro-1-naphthol-7-sulfonic acid (VI') (C.I. 10316); Acid Orange 3 (VI) (C.I. 10383); Acid Yellow 9/Food Yellow 2 (III) (C.I. 13015); Direct Red 45/Food Red 13 (III) (C.I. 14780); Acid Black 52 (III) (C.I. 13711); Acid Yellow 36 (III) (C.I. 13065); Sodium salt of 1-hydroxy-2-(2',4'-xylyl-5-sulfonatoazo)naphthalene-4-sulfonic acid/Food Red 1 (III) (C.I. 14700); Acid Red 14/Food Red 3/Mordant Blue 79 (III) (C.I. 14720); Sodium salt of 4-hydroxy-3-[(2-methoxy-5-nitrophenyl)diaza]-6-(phenylamino)naphthalene-2-sulfonic acid/Acid Brown 4 (III) (C.I. 14805); Acid Orange 7/Pigment Orange 17/Solvent Orange 49 (III) (C.I. 15510); Food Yellow 3/Pigment Yellow 104 (III) (C.I. 15985); Acid Red 27/Food Red 9 (III) (C.I. 16185); Acid Orange 10/Food Orange 4 (III) (C.I. 16230); Acid Red 44 (III) (C.I. 16250); Acid Red 33/Food Red 12 (III) (C.I. 17200); Acid Red 184 (III) (C.I. 15685); Acid Violet 3 (III) (C.I. 19125); Sodium salt of 1-hydroxy-2-(4'-acetamidophenylazo)-8-acetamidonaphthalene-3,6-disulfonic acid/Acid Violet 7/Food Red 11 (III) (C.I. 18055); Acid Red 135 (III) (C.I. 18130); Acid Yellow 27 (IV) (C.I. 19130); Acid Yellow 23/Food Yellow 4 (IV) (C.I. 19140); 4'-(Sulfonato-2",4"-dimethyl)bis(2,6-phenylazo)-1,3-dihydroxybenzene/Acid Orange 24 (III) (C.I. 20170); Sodium salt of 1-amino-2-(4'-nitrophenylazo)-7-phenylazo-8-hydroxynaphthalene-3,6-disulfonic acid/Acid Black 1 (III) (C.I. 20470); (4-((4-methylphenyl)sulfonyloxy)phenylazo)-2,2'-dimethyl-4-((2-hydroxy-5,8-disulfonato)naphthylazo) biphenyl/Acid Red 111 (III') (C.I. 23266); Food Black 2 (III) (C.I. 27755); 1-(4'-Sulfonatophenylazo)-4-((2"-hydroxy-3"-acetylamino-6",8"-disulfonato)naphthylazo)-6-sulfonatonaphthalene (tetrasodium salt)/Food Black 1 (III) (C.I. 25440); Acid Blue 9 (VII) (C.I. 42090); Acid Violet 43 (V) (C.I. 60730); Acid Green 25 (V) (C.I. 61570); Sodium salt of 1-amino-4-cyclohexylamino-9,10-anthraquinone-2-sulfonic acid/Acid Blue 62 (V) (C.I. 62045); Acid Blue 78 (V) (C.I. 62105); Sodium salt of 4-hydroxy-3-((2-methoxyphenyl)azo)-1-naphthalenesulfonic acid/Acid Red 4 (III) (C.I. 14710); 2-Piperidino 5-nitrobenzenesulfonic acid (VI'); 2(4'-N,N(2"-hydroxyethyl)amino-2'-nitro)anilineethanesulfonic acid (VI'); 4-β-hydroxyethylamino-3-nitrobenzenesulfonic acid (VI'); Acid Violet 49 (VII) (C.I. 42640); Acid Blue 7 (VII) (C.I. 42080); Sodium salt of 1,2-dihydroxy-3-sulfoanthraquinone/Mordant Red 3 (V) (C.I. 58005); Sodium salt of 1-amino-9,10-dihydro-9,10-dioxo-4-(phenylamino) 2-anthracenesulfonic acid/Acid Blue 25 (V) (C.I. 62055); Sodium salt of 4-hydroxy-3-((2-methoxyphenyl) azo)-1-naphthalenesulfonic acid/Acid Red 4 (III) (C.I. 14710).

Most of these dyes are described in particular in the Color Index published by The Society of Dyers and Colorists, P.O. Box 244, Perkin House, 82 Grattan Road, Bradford, Yorkshire, BD12 JBN England.

The anionic dyes that are most particularly preferred are the dyes designated in the Color Index under the code C.I. 58005 (monosodium salt of 1,2-dihydroxy-9,10-anthraquinone-3-sulfonic acid), C.I. 60730 (monosodium salt of 2-[(9,10-dihydro-4-hydroxy-9,10-dioxo-1-anthracenyl)amino]-5-methylbenzenesulfonic acid), C.I. 15510 (monosodium salt of 4-[(2-hydroxy-1-naphthalenyl)azo]benzenesulfonic acid), C.I. 15985 (disodium salt of 6-hydroxy-5-[(4-sulfophenyl)azo]-2-naphthalenesulfonic acid), C.I. 17200 (disodium salt of 5-amino-4-hydroxy-3-(phenylazo)-2,7-naphthalenedisulfonic acid), C.I. 20470 (disodium salt of 1-amino-2-(4'-nitrophenylazo)-7-phenylazo-8-hydroxy-3,6-naphthalenedisulfonic acid), C.I. 42090 (disodium salt of N-ethyl-N-[4-[[4-[ethyl(3-sulfophenyl)methyl]amino]phenyl](2-sulfophenyl)methylene]-2,5-cyclohexadien-1-ylidene]-3-sulfobenzenemethanaminium hydroxide, inner salt), C.I. 61570 (disodium salt of 2,2'-[(9,10-dihydro-9,10-dioxo-1,4-anthracenediyl)diimino]bis[5-methyl]benzenesulfonic acid).

Use may also be made of compounds corresponding to the mesomeric or tautomeric forms of structures (III) to (X).

Natural Dyes

The direct dyes a) can be chosen from natural direct dyes.

Among the natural direct dyes that may be used according to the invention, mention may be made of lawsone, juglone, alizarin, purpurin, carminic acid, kermesic acid, purpurogallin, protocatechaldehyde, indigo, isatin, curcumin, spinulosin, apigenidin, orceins, brazilin, brazilein, hematin and hematoxylin. Use may also be made of extracts or decoctions containing these natural dyes and notably henna-based poultices or extracts.

According to one preferred embodiment of the invention, the direct dyes a) have a solubility in water at a temperature of 22° C. and at atmospheric pressure (760 mmHg, i.e. $1.013 \times 10^5$ Pa) of less than 5% by weight, preferably less than 1% by weight and more preferentially less than 0.5% by weight.

b) Compound(s) of Formula (A)

The dyeing process uses a) one or more compounds of formula (A):

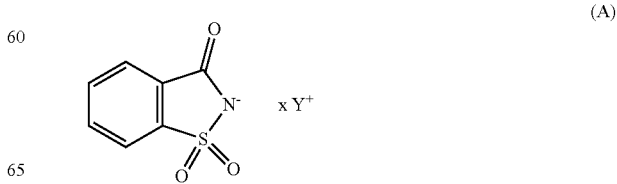

wherein:

Y represents a cationic counterion;

x is a stoichiometric coefficient chosen so as to ensure the electrical neutrality of the compound of formula (A).

The cationic counterion $Y^+$ can be singly charged or multiply charged.

For example, when the cationic counterion is singly charged, the stoichiometric coefficient x will be equal to 1. When the cationic counterion is doubly charged, the stoichiometric coefficient x will be equal to 0.5.

$Y^+$ is chosen from the compounds of formula (Ia), (Ib), (Ic) or (Id) below:

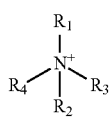

(Ia)

Formula (Ia) wherein $R_1$, $R_2$, $R_3$ and $R_4$ represent, independently of one another:

a hydrogen atom;

a linear or branched, saturated or unsaturated, $C_1$-$C_{12}$, preferably $C_1$-$C_{10}$, hydrocarbon-based group, optionally substituted with one or more group(s) chosen from: hydroxyl, thiol, ($C_1$-$C_6$)alkylthio, amino, —$NH_3^+$, ($C_1$-$C_6$)dialkylamino, ($C_1$-$C_6$)alkylamino, ($C_1$-$C_4$)alkoxyl, carboxyl, carboxylate, —$SO_3H$, —$SO_3^-$, —C(O)$NH_2$, —NHC(NH)—$NH_2$, —C(O)$OR^a$, —OC(O)—$R^a$, —C(O)$NHR^a$, —NH—C(O)—$R_a$, phenyl, indolyl, phenol, furan, guaiacol, imidazole or guanine and/or optionally interrupted by one or more group(s) chosen from —C(O)—, —$NR^b$—, —C($NR^b$)—, —OC(O)—, —C(O)O—, —C(O)$NR^b$— or —$NR^bC(O)$—;

$R^a$ representing a ($C_1$-$C_4$)alkyl group; and $R^b$ representing a hydrogen atom or a ($C_1$-$C_4$)alkyl group, preferably a hydrogen atom; it being understood that the overall charge of the compounds of formula (Ia) is positive;

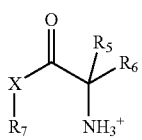

(Ib)

formula (Ib) wherein:

X represents an oxygen atom or an $NR^b$ group;

$R_5$, $R_6$ and $R_7$ represent independently of one another:

a hydrogen atom;

a carboxyl or carboxylate group;

a —C(O)$NH_2$ group;

a linear or branched, saturated or unsaturated, $C_1$-$C_{12}$, preferably $C_1$-$C_{10}$, hydrocarbon-based group, optionally substituted with one or more group(s) chosen from: hydroxyl, thiol, ($C_1$-$C_6$)alkylthio, amino, —$NH_3$+, ($C_1$-$C_6$)dialkylamino, ($C_1$-$C_6$)alkylamino, ($C_1$-$C_4$)alkoxyl, carboxyl, carboxylate, —$SO_3H$, —$SO_3^-$, —C(O)$NH_2$, —NHC(NH)—$NH_2$, —C(O)$OR^a$, —OC(O)—$R^a$, —C(O)$NHR^a$, —NH—C(O)—$R^a$, phenyl, indolyl, phenol, furan, guaiacol, imidazole or guanine and/or optionally interrupted by one or more group(s) chosen from —C(O)—, —$NR^b$—, —C($NR^b$)—, —OC(O)—, —C(O)O—, —C(O)$NR^b$— or —$NR^bC(O)$—;

$R^a$ representing a ($C_1$-$C_4$)alkyl group; and $R^b$ representing a hydrogen atom or a ($C_1$-$C_4$)alkyl group, preferably a hydrogen atom; it being understood that the overall charge of the compounds of formula (Ib) is positive;

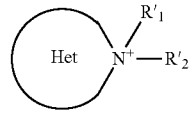

(Ic)

formula (Ic) wherein:

Het represents a cationic saturated heterocyclic group comprising:

from 5 to 10 ring members, preferably 5 or 6 ring members; and in addition to the ammonium bearing $R'_1$ and $R'_2$, optionally one or two atoms chosen from nitrogen and/or oxygen atoms, preferably a nitrogen atom;

the heterocyclic group being optionally substituted with one or more group(s) $R'_3$;

$R'_1$ and $R'_2$, which may be identical or different, represent a hydrogen atom or a linear or branched, saturated or unsaturated, $C_1$-$C_{12}$ hydrocarbon-based group, optionally substituted with one or more group(s) chosen from: hydroxyl, amino, ($C_1$-$C_6$)dialkylamino, ($C_1$-$C_6$)alkylamino, carboxyl, carboxylate, carbamide, ($C_1$-$C_4$) alkoxyl, —$SO_3H$, —$SO_3^-$ or phenyl;

$R'_3$, which may be identical or different, represent a hydroxyl group, an amino group, a —C(O)$OR'_4$ group, an —OC(O)—$R'_4$ group, a —C(O)$NHR'_4$ group, an —NH—C(O)—$R'_4$ group, a linear or branched, saturated or unsaturated, $C_1$-$C_{12}$ hydrocarbon-based group, optionally substituted with one or more group(s) chosen from: hydroxyl, amino, ($C_1$-$C_6$)dialkylamino, ($C_1$-$C_6$)alkylamino, carboxyl, carboxylate, carbamide, ($C_1$-$C_4$)alkoxyl, —$SO_3H$, —$SO_3^-$ or phenyl;

$R'_4$ represents a hydrogen atom, a linear or branched, saturated or unsaturated, $C_1$-$C_{12}$ hydrocarbon-based group, optionally substituted with one or more group(s) chosen from hydroxyl, amino, ($C_1$-$C_6$)dialkylamino or ($C_1$-$C_6$)alkylamino;

it being understood that the overall charge of the compounds of formula (Ic) is positive;

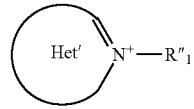

(Id)

formula (Id) wherein:

Het' represents a cationic aromatic unsaturated heterocyclic group comprising:

from 5 to 10 ring members, preferably 5 or 6 ring members; and in addition to the ammonium bearing $R''_1$, optionally one or two atoms chosen from nitrogen or oxygen atoms, preferably a nitrogen atom;

said heterocyclic group being optionally substituted with one or more group(s) $R''_2$;

R"$_1$ represents a linear or branched, saturated or unsaturated, C$_1$-C$_{12}$ hydrocarbon-based group, optionally substituted with one or more group(s) chosen from hydroxyl, amino, (C$_1$-C$_6$)dialkylamino, (C$_1$-C$_5$)alkylamino, carboxyl, carboxylate, carbamide, (C$_1$-C$_4$)alkoxyl, —SO$_3$H, —SO$_3^-$ or phenyl; and R"$_2$, which may be identical or different, represent a hydroxyl group, an amino group, or a linear or branched, saturated or unsaturated, C$_1$-C$_{12}$ hydrocarbon-based group, optionally substituted with one or more group(s) chosen from hydroxyl, amino, (C$_1$-VS$_6$)dialkylamino, (C$_1$-VS$_6$)alkylamino, carboxyl, carboxylate, carbamide, (C$_1$-VS$_4$)alkoxyl, —SO$_3$H, —SO$_3^-$ or phenyl;

it being understood that the overall charge of the compounds of formula (Id) is positive.

According to one particular embodiment, Y$^+$ is chosen from the compounds of formula (Ia) as defined above, preferably from the compounds of formula (Ia) wherein R$_1$, R$_2$ and R$_3$ each represent a hydrogen atom and R$_4$ is as defined hereinbefore.

According to one particular embodiment, Y$^+$ is chosen from the compounds of formula (Ib) as defined above, preferably from the compounds of formula (Ib) wherein:

R$_5$ represents a hydrogen atom;

R$_6$ represents a linear or branched (C$_1$-C$_4$)alkyl group, optionally substituted with one or more group(s) chosen from: hydroxyl, thiol, (C$_1$-C$_6$)alkylthio, amino, —NH$_3^+$, (C$_1$-C$_6$)dialkylamino, (C$_1$-C$_6$)alkylamino, (C$_1$-C$_4$)alkoxyl, carboxyl, carboxylate, —SO$_3$H, —SO$_3^-$, —C(O)NH$_2$, —NHC(NH)—NH$_2$, —C(O)OR$^a$, —OC(O)—R$^a$, —C(O)NHR$^a$, —NH—C(O)—R$^a$, phenyl, indolyl, phenol, furan, guaiacol, imidazole or guanine and/or optionally interrupted by one or more group(s) chosen from —C(O)—, —NR$^b$—, —C(NR$^b$)—, —OC(O)—, —C(O)O—, —C(O)NR$^b$— or —NR$^b$C(O)—;

R$^a$ representing a (C$_1$-C$_4$)alkyl group; and

R$^b$ representing a hydrogen atom or a (C$_1$-C$_4$)alkyl group, preferably a hydrogen atom;

R$_7$ represents a linear or branched (C$_1$-C$_4$)alkyl group, optionally substituted with one or more hydroxyl group(s);

it being understood that the overall charge of the compounds of formula (Ib) is positive.

According to one particular embodiment, Y$^+$ is chosen from the compounds of formula (Ic) as defined above, preferably from the compounds of formula (Ic) wherein:

Het is as defined above;

R'$_1$ and R'$_2$, which may be identical or different, represent a hydrogen atom or a linear or branched (C$_1$-C$_4$)alkyl group, optionally substituted with one or more group(s) chosen from: hydroxyl, amino, (C$_1$-C$_6$)dialkylamino, (C$_1$-C$_6$)alkylamino, carboxyl, carboxylate, carbamide, (C$_1$-C$_4$)alkoxyl, —SO$_3$H, —SO$_3^-$ or phenyl;

R'$_3$, which may be identical or different, represent a group —C(O)OR'$_4$, a group —O—C(O)—R'$_4$, a group —C(O)NHR'$_4$ or a group —NH—C(O)—R'$_4$;

R'$_4$ represents a (C$_1$-C$_{12}$)alkyl group, optionally substituted with one or more group(s) chosen from hydroxyl, amino, (C$_1$-C$_6$)dialkylamino or (C$_1$-C$_6$)alkylamino;

it being understood that the overall charge of the compounds of formula (Ic) is positive.

According to one particular embodiment, Y$^+$ is chosen from the compounds of formula (Id) as defined above, preferably from the compounds of formula (Id) wherein:

Het' is as defined above;

R"'$_1$ represents a linear or branched, saturated or unsaturated, unsubstituted C$_1$-C$_6$, preferably C$_1$-C$_4$, hydrocarbon-based group;

R"'$_2$, which may be identical or different, represent a hydroxyl group or a linear or branched, unsubstituted (C$_1$-C$_6$)alkyl group, preferably a linear or branched, unsubstituted (C$_1$-C$_4$)alkyl group.

According to one preferred embodiment, Y$^+$ is chosen from the following compounds 1 to 69:

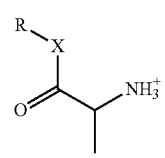

1

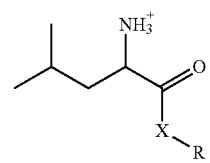

2

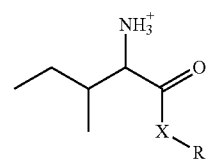

3

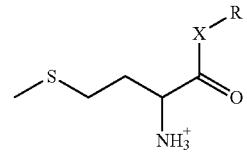

4

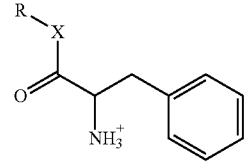

5

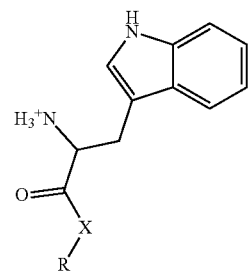

6

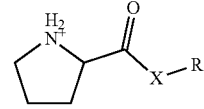

7

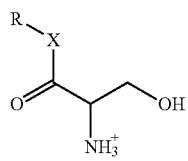
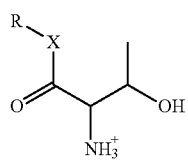
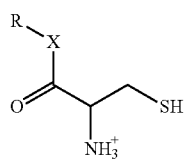
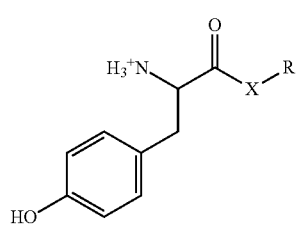
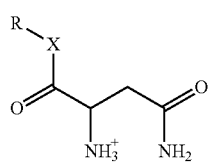
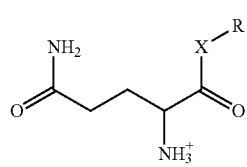
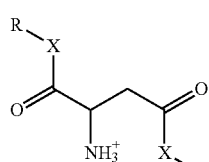
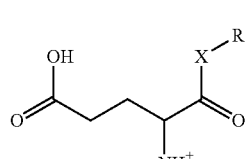
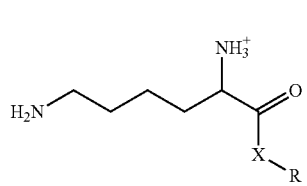
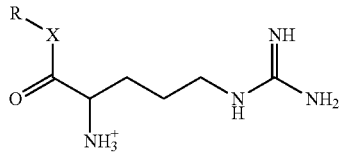
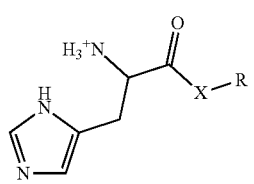
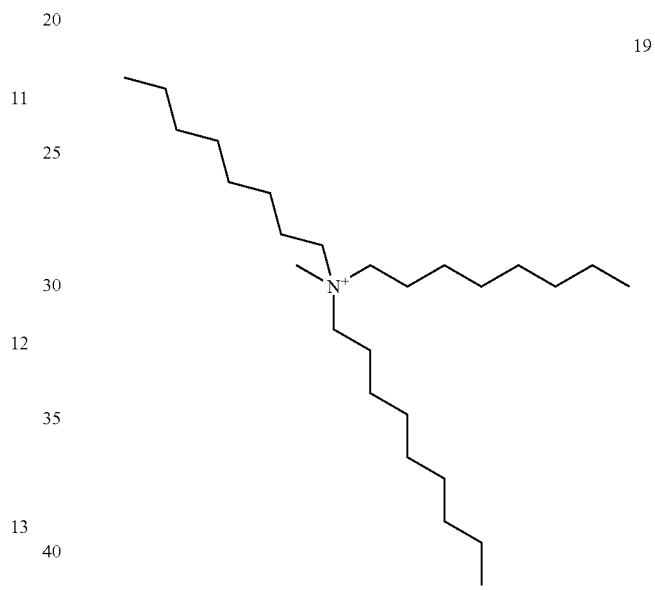
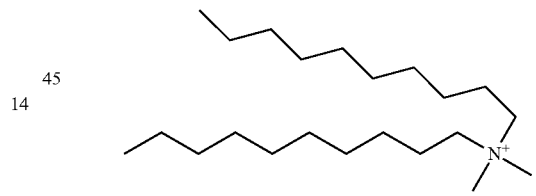
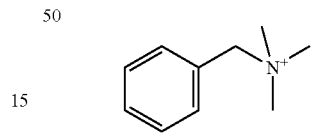
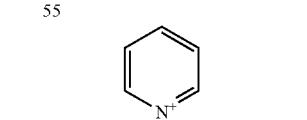
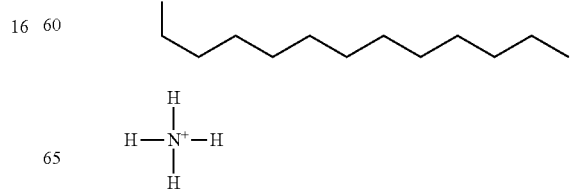

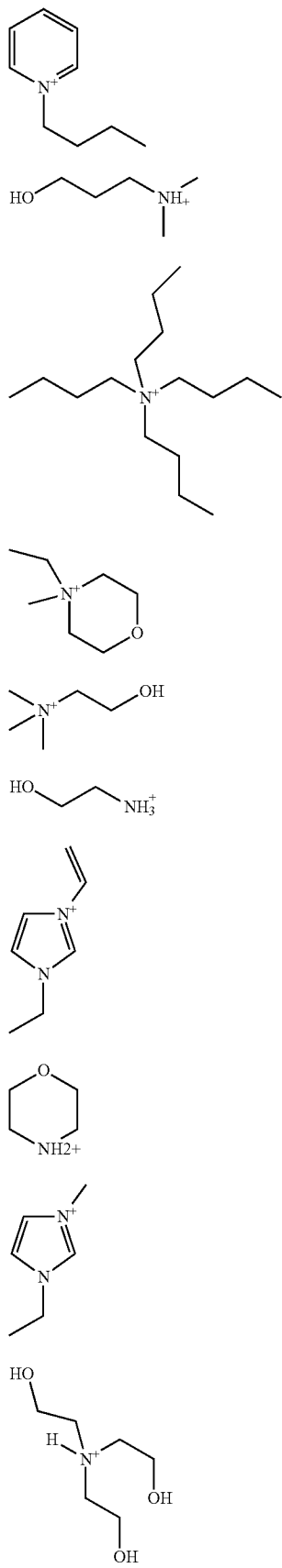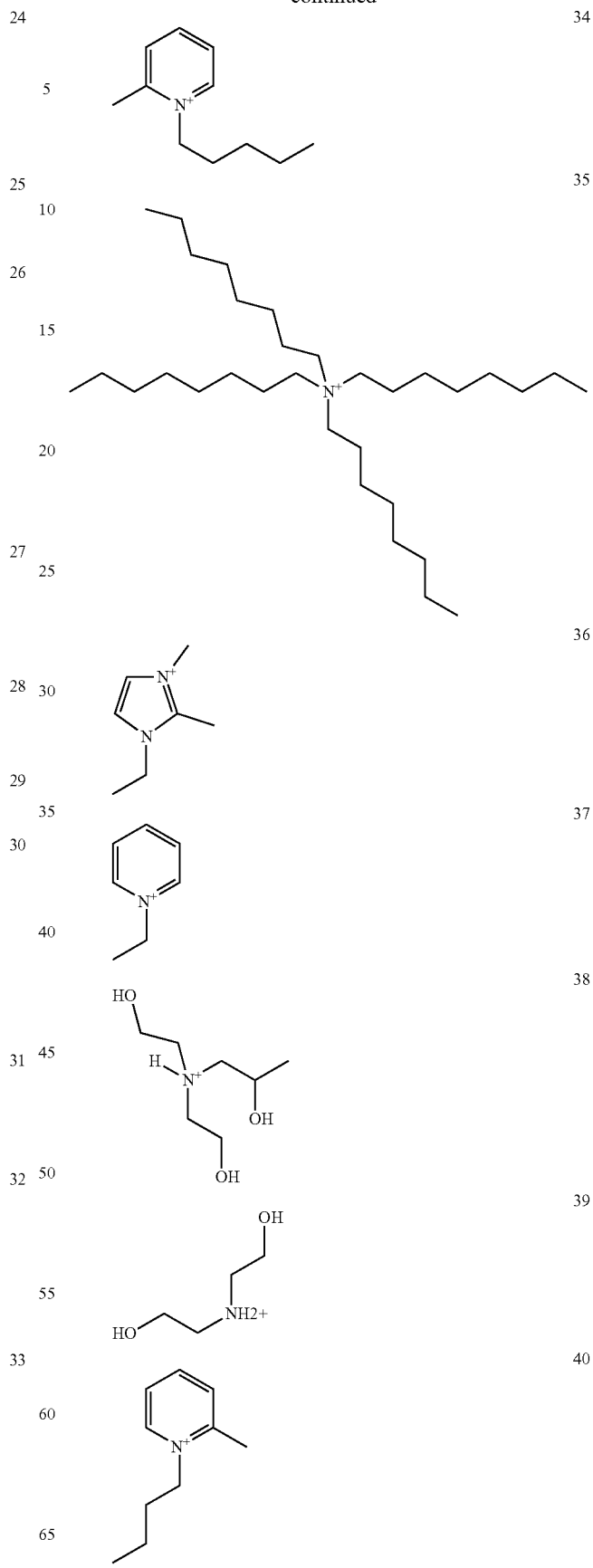

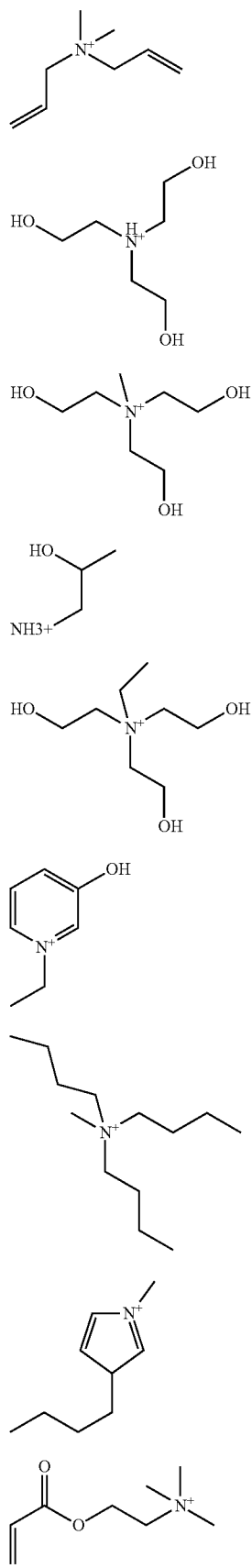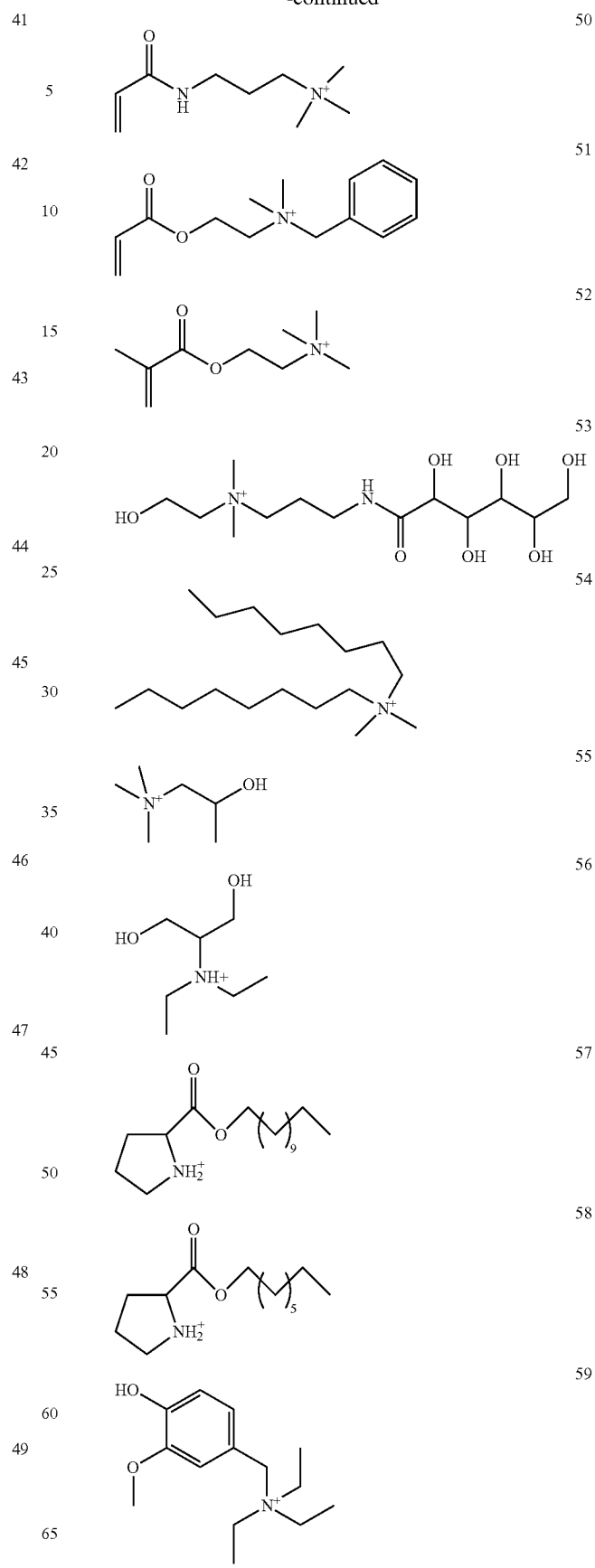

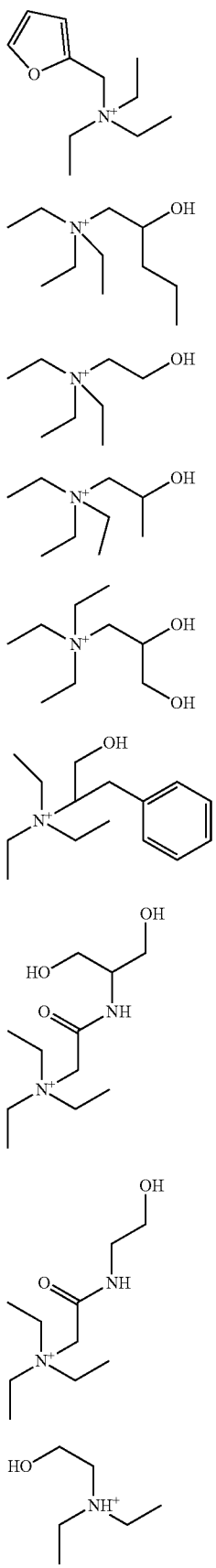

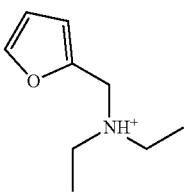

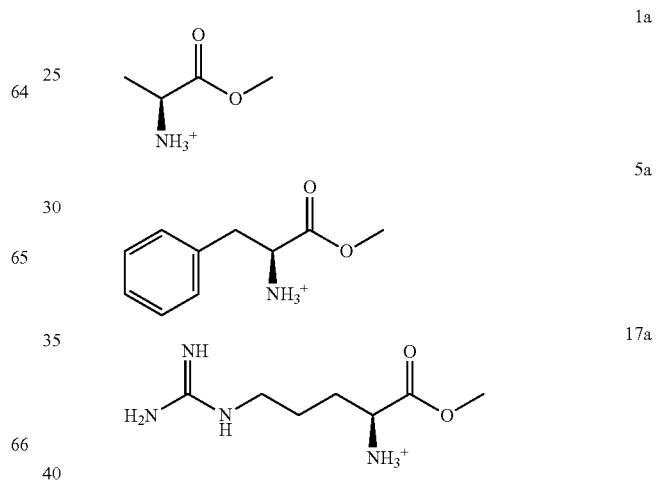

with R representing a (C$_1$-C$_4$)alkyl group optionally substituted with one or more hydroxyl group(s) and X representing an oxygen atom or an NR$^b$ group, R$^b$ representing a hydrogen atom or a (C$_1$-C$_4$)alkyl group, preferably a hydrogen atom.

More preferentially, Y$^+$ is chosen from the compounds 1, 5, 17 and 32.

Even more preferentially, Y$^+$ is chosen from the compound 32 and the following compounds 1a, 5a and 17a:

Other Characteristics of the Dyeing Process

The dyeing process uses the ingredients a) and b) as described above. The ingredients a) and b) are applied simultaneously or sequentially to the keratin fibers.

According to a first embodiment of the invention, the ingredients a) and b) are applied simultaneously to the keratin fibers. According to one variant of this first embodiment, the process comprises a step of applying to the keratin fibers a composition comprising:
  a) one or more direct dyes as defined above; and
  b) one or more compounds of formula (A) as defined above.

Preferably, the composition comprising a) and b) is aqueous.

More preferentially, the composition comprises only the ingredients a), b) and water.

According to a second embodiment of the invention, the ingredients a) and b) are applied sequentially to the keratin fibers. According to one variant of this second embodiment, the process comprises i) a first step of applying to the keratin fibers a composition comprising a) one or more direct dyes as defined above, then ii) a second step of applying to the keratin fibers a composition comprising b) one or more compounds of formula (A) as defined above.

According to one variant of this second embodiment, the process comprises i) a first step of applying to the keratin fibers a composition comprising b) one or more compounds of formula (A) as defined above, then ii) a second step of applying to the keratin fibers a composition comprising a) one or more direct dyes as defined above.

Preferably, the composition comprising a) and the composition comprising b) are aqueous.

The direct dye(s) a) as defined above are present in the composition comprising them preferably in a content ranging from 0.001% to 10% by weight, more preferentially from 0.05% to 5% by weight, even more preferentially from 0.3% to 3% by weight relative to the total weight of the composition comprising them.

The compound(s) of formula (A) as defined above are present in the composition comprising them preferably in a content ranging from 1% to 99.5% by weight, more preferentially from 3% to 90% by weight, even more preferentially from 10% to 80% by weight, most preferentially from 20% to 60% by weight, better still from 20% to 50% by weight, and even better still from 20% to 40% by weight relative to the total weight of the composition comprising them.

Chemical Oxidizing Agents:

The composition(s) can also comprise at least one chemical oxidizing agent.

The term "chemical oxidizing agent" is intended to mean an oxidizing agent other than atmospheric oxygen.

Preferably, the chemical oxidizing agent is chosen from hydrogen peroxide, urea peroxide, peroxygenated salts, peracids and precursors thereof, and mixtures thereof.

More preferentially, the chemical oxidizing agent is chosen from hydrogen peroxide, peroxygenated salts, and mixtures thereof.

Even more preferentially, the chemical oxidizing agent is chosen from hydrogen peroxide, persulfates, perborates or percarbonates of alkali metals or alkaline-earth metals or of ammonium, and mixtures thereof.

Most preferentially, the chemical oxidizing agent is hydrogen peroxide.

Examples of peroxygenated salts that may be mentioned include sodium, potassium or ammonium persulfates and mixtures thereof.

According to one particular embodiment, the composition(s) can comprise a mixture of peroxygenated salt and of hydrogen peroxide.

The composition(s) can comprise a total content of chemical oxidizing agents ranging from 0.5% to 20%, preferably ranging from 1% to 15% by weight relative to the total weight of the composition comprising them.

The composition(s) are cosmetic, i.e. they are in a cosmetic medium.

The term "cosmetic medium" is intended to mean a medium that is suitable for dyeing keratin fibers, also known as a dye support, which is a cosmetic medium generally formed from water or a mixture of water and one or more organic solvents or a mixture of organic solvents.

Preferably, the composition(s) comprise water in an amount ranging from 5% to 95% relative to the total weight of the composition.

More preferentially, the composition(s) of the invention do not comprise any ingredients other than a) and b).

The term "organic solvent" is intended to mean an organic substance that is capable of dissolving another substance without chemically modifying it.

Examples of organic solvents that may be mentioned include lower $C_1$-$C_4$ alkanols, such as ethanol and isopropanol; polyols and polyol ethers, for instance 2-butoxyethanol, propylene glycol, propylene glycol monomethyl ether and diethylene glycol monoethyl ether and monomethyl ether, and also aromatic alcohols, for instance benzyl alcohol or phenoxyethanol, and mixtures thereof.

The organic solvents are present in proportions preferably ranging from 0.1% 40% by weight, more preferentially from 1% to 30% by weight, even more preferentially from 5% to 25% by weight, relative to the total weight of the composition.

The composition(s) may also comprise one or more compounds that are liquid at ambient temperature and at atmospheric pressure and that are different than the compounds of formula (A) of the invention. The liquid compound is preferably a solvent and in particular a solvent chosen from water, aliphatic $C_1$-$C_4$ alcohols such as ethanol and isopropanol, organic solvents which are soluble or dispersible in water such as acetone, propylene carbonate, benzyl alcohol, glycol ether derivatives, polyols such as glycerol, propylene glycol and polyethylene glycols. More preferentially, the liquid compound is a polar solvent, even more preferentially a polar protic solvent.

pH

The pH of the composition(s) comprising the ingredients a) and/or b) is preferably from 3 to 12, more preferentially from 5 to 10, even more preferentially from 6 to 9.5.

The pH of this or these compositions may be adjusted with acidifying or basifying agents conventionally used in cosmetics.

Among the acidifying agents, examples that may be mentioned include organic or mineral acids.

The term "mineral acid" is intended to mean any acid derived from a mineral compound.

Among the mineral acids, mention may be made of hydrochloric acid, orthophosphoric acid, sulfuric acid, sulfonic acids and nitric acid.

The term "organic acid" is intended to mean any acid derived from an organic compound.

Among the organic acids, mention may be made of acetic acid, tartaric acid, citric acid, lactic acid and sulfonic acids.

Use may notably be made of mineral or organic acids such as hydrochloric acid, orthophosphoric acid, sulfuric acid, carboxylic acids, for instance acetic acid, tartaric acid, citric acid or lactic acid, and sulfonic acids.

Among the alkaline agents, examples that may be mentioned include aqueous ammonia, alkali metal carbonates, alkanolamines, such as monoethanolamine, diethanolamine and triethanolamine and derivatives thereof, sodium hydroxide, potassium hydroxide and the compounds of formula (B) below:

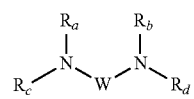

(B)

formula (B) wherein W is a $(C_1$-$C_6)$alkylene group optionally substituted with one or more hydroxyl groups; $R_a$, $R_b$, $R_c$ and $R_d$, which may be identical or different, represent a hydrogen atom or a $(C_1$-$C_4)$alkyl group optionally substituted with one or hydroxyl groups. Preferably, the pH modifiers may be chosen from alkaline agents, such as aqueous ammonia, monoethanolamine, diethanolamine, triethanolamine, 1,3-propanediamine or an alkaline hydroxide, such as 2-amino-2-methyl-1-propanol, or else acidifying agents, such as phosphoric acid or hydrochloric acid.

The composition(s) comprising the ingredients a) and/or b) may be in liquid form, in the form of a serum, in thickened form, in particular a gel, a cream, a wax or a paste, or in foam form.

The composition(s) of the invention may also comprise one or more additional compounds other than the ingredients a) and/or b).

These additional compounds are generally chosen from nonionic, anionic, cationic or amphoteric surfactants, cationic, anionic, nonionic or zwitterionic, associative or non-associative thickening polymers of natural or synthetic origin, silicones in the form of oils, gums or resins or non-silicone plant, mineral or synthetic oils, UV-screening agents, fillers, such as nacres and metal oxides such as titanium dioxides, clays, fragrances, peptizers, vitamins and preserving agents.

The composition(s) may be applied to wet or dry keratin fibers.

Preferably, the application to the keratin fibers of the composition(s) comprising the ingredients a) and/or b) is carried out at ambient temperature, i.e. at a temperature of between 25° C. and 30° C.

According to one advantageous variant of the invention, after sequential or simultaneous application of the ingredients a) and b), the keratin fibers are rinsed, optionally shampooed and then dried or left to dry, for example at a temperature of greater than or equal to 30° C.

According to a particular embodiment, this temperature is greater than 40° C. According to a particular embodiment, this temperature is greater than 45° C. and less than 220° C.

Preferably, if the keratin fibers are dried, they are dried, in addition to a supply of heat, with a flow of air.

During the drying, a mechanical action may be exerted on the fibers, such as combing, brushing or running the fingers through. This operation may similarly be carried out once the keratin fibers have dried, naturally or otherwise.

The drying step can be carried out with a drying device such as a hood, a hairdryer, a smoothing iron or a climazone.

The drying step can be carried out with a hood or a hairdryer, the drying temperature ranging from 40° C. to 110° C. and preferably from 50° C. to 90° C.

Once the drying is complete, final rinsing or shampooing may optionally be performed.

The composition(s) are applied to the wet or dry keratin fibers, preferably with a weight ratio of the amount of composition applied relative to the amount of hair ranging from 0.1 to 10 and more particularly ranging from 0.2 to 5.

Composition

According to a second aspect, a subject of the present invention is a composition comprising:
a) optionally one or more direct dyes; and
b) one or more compounds of formula (A) as defined above.

Preferably, the composition according to the present invention comprises:
a) one or more direct dyes; and
b) one or more compounds of formula (A) as defined above.

The optional technical characteristics relating to this composition which are described in the context of the process of the invention also apply to the composition as such.

Kit

According to a third aspect, a subject of the present invention is a multicompartment device or kit, comprising at least a first compartment which comprises one or more direct dyes as defined above, and at least a second compartment which comprises one or more compounds of formula (A) as defined above.

EXAMPLES

The examples that follow will allow the invention to be understood more clearly, without, however, being limiting in nature.

Example 1

Dyes Evaluated:

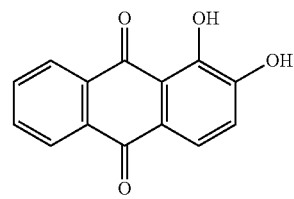

Dye 1

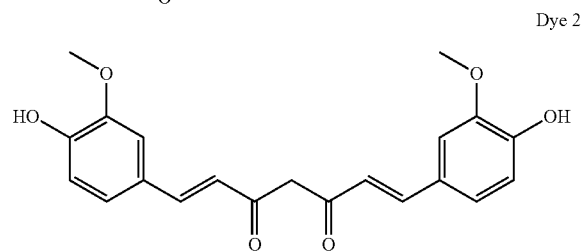

Dye 2

Compounds A Tested:

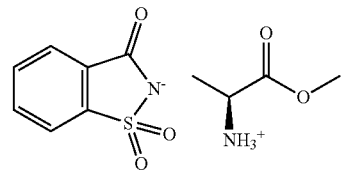

Compound 1

Compound 2

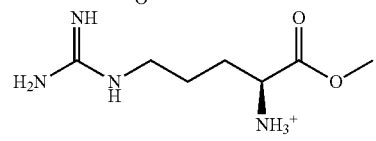

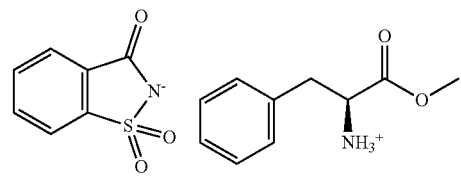

Compound 3

-continued

Compound 4

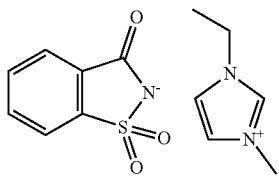

Preparation of the Compositions:

The comparative compositions (Comp 1 or 2) and the compositions according to the invention (Inv 1.1 to 1.7 and 2.1 to 2.6) were prepared while adhering to the amounts described in the tables below:

TABLE 1

| Ingredients | Comp 1 | Inv 1.1 | Inv 1.2 | Inv 1.3 | Inv 1.4 | Inv 1.5 | Inv. 1.6 | Inv 1.7 |
|---|---|---|---|---|---|---|---|---|
| Dye 1 (g %) | 0.5 | 0.5 | 0.5 | 0.5 | 0.5 | 0.5 | 0.5 | 0.5 |
| Compound 1 (g %) | — | 10 | — | — | — | — | — | — |
| Compound 2 (g %) | — | — | 10 | 20 | — | — | — | — |
| Compound 3 (g %) | — | — | — | — | 10 | 20 | — | — |
| Compound 4 (g %) | — | — | — | — | — | — | 10 | 20 |
| Aqueous ammonia (20% solution) | qs pH = 9.5 | qs pH = 9.5 | qs pH = 9.5 | qs pH = 9.5 | qs pH = 9.5 | qs pH = 9.5 | qs pH = 9.5 | qs pH = 9.5 |
| Water | qs 100 g | qs 100 g | qs 100 g | qs 100 g | qs 100 g | qs 100 g | qs 100 g | qs 100 g |

TABLE 2

| Ingredients | Comp 2 | Inv 2.1 | Inv 2.2 | Inv 2.3 | Inv 2.4 | Inv 2.5 | Inv 2.6 |
|---|---|---|---|---|---|---|---|
| Dye 2 (g %) | 0.5 | 0.5 | 0.5 | 0.5 | 0.5 | 0.5 | 0.5 |
| Compound 2 (g %) | — | 10 | 20 | — | — | — | — |
| Compound 3 (g %) | — | — | — | 10 | 20 | — | — |
| Compound 4 (g %) | — | — | — | — | — | 10 | 20 |
| Aqueous ammonia (20% solution) | qs pH = 9.5 | qs pH = 9.5 | qs pH = 9.5 | qs pH = 9.5 | qs pH = 9.5 | qs pH = 9.5 | qs pH = 9.5 |
| Water | qs 100 g | qs 100 g | qs 100 g | qs 100 g | qs 100 g | qs 100 g | qs 100 g |

Application on Locks:
Protocol:

2 g of comparative composition (Comp x) or composition according to the invention (Inv x) are applied to 1 g of hair containing 90% natural white hair at 33° C. for 30 minutes. The hair is then rinsed, shampooed and dried.

Colorimetric Measurements:

The color build-up ($\Delta E^*$) was evaluated in the CIE $L^*a^*b^*$ system using a Minolta Spectrophotometer CM3610A colorimeter (illuminant D65). In this $L^*a^*b^*$ system, $L^*$ represents the intensity of the color, $a^*$ indicates the shade of the color on the green/red color axis and $b^*$ indicates the shade of the color on the blue/yellow color axis. The lower the value of $L^*$, the darker or more intense the color. The higher the value of $a^*$, the redder the shade, and the higher the value of $b^*$, the bluer the shade.

In the table below, the value of $\Delta E^*$ is calculated from the $L^*a^*b^*$ values according to the following equation:

$$\Delta E^* = \sqrt{(L^*-L_0^*)^2 + (a^*-a_0^*)^2 + (b^*-b_0^*)^2}$$

In the equation, $L^*$, $a^*$ and $b^*$ represent the values measured on the locks after treatment by means of the protocol above, and $L_0^*$, $a_0^*$ and $b_0^*$ represent the values measured on control locks that were not treated.

The higher the $\Delta E^*$ value, the better the color build-up or variation.

Dyeing Results:

The various build-up results obtained are given in the tables below:

TABLE 3

|  | $\Delta E^*$ build-up |
|---|---|
| Comparative 1 | 16.3 |
| Invention 1.1 | 28.1 |
| Invention 1.2 | 30.4 |
| Invention 1.3 | 26.6 |
| Invention 1.4 | 24.5 |
| Invention 1.5 | 20.7 |
| Invention 1.6 | 29 |
| Invention 1.7 | 28.6 |

TABLE 4

|  | $\Delta E^*$ build-up |
|---|---|
| Comparative 2 | 6.1 |
| Invention 2.1 | 11.7 |
| Invention 2.2 | 20.3 |
| Invention 2.3 | 13.7 |
| Invention 2.4 | 18.1 |
| Invention 2.5 | 13.2 |
| Invention 2.6 | 15.3 |

It is seen from the above results that the color build-up is significantly improved by the presence of a compound of formula (A) according to the present invention.

The invention claimed is:

1. A method of dyeing keratin fibers, comprising applying to the keratin fibers:
   (a) at least one direct dye; and
   (b) at least one compound of formula (A):

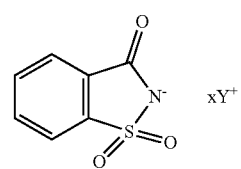

(A)

wherein:

$Y^+$, which can be the same or different, represents a cationic counterion chosen from compounds of formula (Ia), (Ib), (Ic), and/or (Id) below:

(Ia)

wherein in formula (Ia), $R_1$, $R_2$, $R_3$ and $R_4$ are independently chosen from:
- a hydrogen atom; and/or
- a linear or branched, saturated or unsaturated, $C_1$-$C_{12}$ hydrocarbon-based group, optionally: (i) substituted with one or more groups chosen from hydroxyl, thiol, ($C_1$-$C_6$)alkylthio, amino, —$NH_3^+$, ($C_1$-$C_6$)dialkylamino, ($C_1$-$C_6$)alkylamino, ($C_1$-$C_4$)alkoxyl, carboxyl, carboxylate, —$SO_3H$, —$SO_3^-$, —C(O)$NH_2$, —NHC(NH)—$NH_2$, —C(O)$OR^a$, —OC(O)—$R^a$, —C(O)$NHR^a$, —NH—C(O)—$R^a$, phenyl, indolyl, phenol, furan, guaiacol, imidazole, or guanine; or (ii) interrupted by one or more group(s) chosen from —C(O)—, —$NR^b$—, —C($NR^b$)—, —OC(O)—, —C(O)O—, —C(O)$NR^b$— or —$NR^b$C(O)—, with:
  - $R^a$ representing a ($C_1$-$C_4$)alkyl group; and
  - $R^b$ representing a hydrogen atom or a ($C_1$-$C_4$)alkyl group;

wherein the overall charge of the compounds of formula (Ia) is positive;

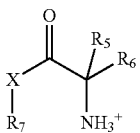

(Ib)

wherein in formula (Ib):
- X represents an oxygen atom or an $NR^b$ group, $R^b$ representing a hydrogen atom or a ($C_1$-$C_4$)alkyl group;
- $R_5$, $R_6$ and $R_7$ represent independently of one another:
  - a hydrogen atom;
  - a carboxyl or carboxylate group;
  - a —C(O)$NH_2$ group; and/or
  - a linear or branched, saturated or unsaturated, $C_1$-$C_{12}$ hydrocarbon-based group, optionally: (i) substituted with one or more groups chosen from hydroxyl, thiol, ($C_1$-$C_6$)alkylthio, amino, —$NH_3^+$, ($C_1$-$C_6$)dialkylamino, ($C_1$-$C_6$)alkylamino, ($C_1$-$C_4$)alkoxyl, carboxyl, carboxylate, —$SO_3H$, —$SO_3^-$, —C(O)$NH_2$, —NHC(NH)—$NH_2$, —C(O)$OR^a$, —OC(O)—$R^a$, —C(O)$NHR^a$, —NH—C(O)—$R^a$, phenyl, indolyl, phenol, furan, guaiacol, imidazole, or guanine; or (ii) interrupted by one or more group(s) chosen from —C(O)—, —$NR^b$—, —C($NR^b$)—, —OC(O)—, —C(O)O—, —C(O)$NR^b$— or —$NR^b$C(O)—, with:
    - $R^a$ representing a ($C_1$-$C_4$)alkyl group; and
    - $R^b$ representing a hydrogen atom or a ($C_1$-$C_4$)alkyl group;

wherein the overall charge of the compounds of formula (Ib) is positive;

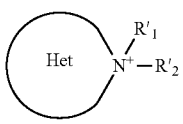

(Ic)

wherein in formula (Ic):
Het represents a cationic saturated heterocyclic group comprising:
- from 5 to 10 ring members; and
- in addition to the ammonium bearing $R'_1$ and $R'_2$, optionally also bearing one or two atoms chosen from nitrogen and/or oxygen atoms;

the heterocyclic group being optionally substituted with one or more groups $R'_3$, which is independently chosen from a hydroxyl group, an amino group, a —C(O)$OR'_4$ group, an —OC(O)—$R'_4$ group, a —C(O)$NHR'_4$ group, an —NH—C(O)—$R'_4$ group, a linear or branched, saturated or unsaturated, $C_1$-$C_{12}$ hydrocarbon-based group, optionally substituted with one or more groups chosen from: hydroxyl, amino, ($C_1$-$C_6$)dialkylamino, ($C_1$-$C_6$)alkylamino, carboxyl, carboxylate, carbamide, ($C_1$-$C_4$)alkoxyl, —$SO_3H$, —$SO_3^-$ or phenyl;

$R'_4$ representing a hydrogen atom, a linear or branched, saturated or unsaturated, $C_1$-$C_{12}$ hydrocarbon-based group, optionally substituted with one or more groups chosen from hydroxyl, amino, ($C_1$-$C_6$)dialkylamino or ($C_1$-$C_6$)alkylamino; and $R'_1$ and $R'_2$ are independently chosen from a hydrogen atom or a linear or branched, saturated or unsaturated, $C_1$-$C_{12}$ hydrocarbon-based group, optionally substituted with one or more groups chosen from hydroxyl, amino, ($C_1$-$C_6$)dialkylamino, ($C_1$-$C_6$)alkylamino, carboxyl, carboxylate, carbamide, ($C_1$-$C_4$)alkoxyl, —$SO_3H$, —$SO_3^-$, or phenyl;

wherein the overall charge of the compounds of formula (Ic) is positive;

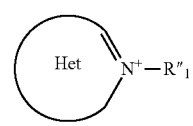

(Id)

wherein in formula (Id):
Het' represents a cationic aromatic unsaturated heterocyclic group comprising:
- from 5 to 10 ring members; and
- in addition to the ammonium bearing $R''_1$, optionally also bearing one or two atoms chosen from nitrogen and/or oxygen atoms;

said heterocyclic group being optionally substituted with one or more groups $R''_2$ which is independently chosen from a hydroxyl group, an amino group, or a linear or branched, saturated or unsaturated, C1-C12 hydrocarbon-based group, optionally substituted with one or more group(s) chosen from hydroxyl, amino, (C1-C6)dialkylamino, (C1-C6)alkylamino, carboxyl, carboxylate, carbamide, (C1-C4)alkoxyl, —SO3H, —SO3– or phenyl; and $R''_1$ represents a linear or branched, saturated or unsaturated, $C_1$-$C_{12}$ hydrocarbon-based group, optionally substituted with one or more groups chosen from hydroxyl, amino, ($C_1$-$C_6$)dialkylamino, ($C_1$-$C_6$)alkylamino, carboxyl, carboxylate, carbamide, ($C_1$-$C_4$)alkoxyl, —$SO_3H$, —$SO_3^-$, or phenyl;

wherein the overall charge of the compounds of formula (Id) is positive; and x is a stoichiometric coefficient configured to balance the electrical neutrality of the compound of formula (A);

wherein a) and b) are applied simultaneously or sequentially to the keratin fibers.

2. The method according to claim 1, wherein $Y^+$ is chosen from compounds of formula (Ia).

3. The method according to claim 1, wherein $Y^+$ is chosen from compounds of formula (Ib), wherein:
$R_5$ represents a hydrogen atom;
$R_6$ represents a linear or branched ($C_1$-$C_4$)alkyl group, optionally: (i) substituted with one or more groups chosen from hydroxyl, thiol, ($C_1$-$C_6$)alkylthio, amino, —$NH_3^+$, ($C_1$-$C_6$)dialkylamino, ($C_1$-$C_6$)alkylamino, ($C_1$-$C_4$)alkoxyl, carboxyl, carboxylate, —$SO_3H$, —$SO_3^-$, —C(O)$NH_2$, —NHC(NH)—$NH_2$, —C(O)OR$^a$, —OC(O)—R$^a$, —C(O)NHR$^a$, —NH—C(O)—R$^a$, phenyl, indolyl, phenol, furan, guaiacol, imidazole, or guanine; or (ii) interrupted by one or more groups chosen from —C(O)—, —NR$^b$—, —C(NR$^b$)—, —OC(O)—, —C(O)O—, —C(O)NR$^b$— or —NR$^b$C(O)—, with:
R$^a$ representing a ($C_1$-$C_4$)alkyl group; and
R$^b$ representing a hydrogen atom or a ($C_1$-$C_4$)alkyl group; and
$R_7$ represents a linear or branched ($C_1$-$C_4$)alkyl group, optionally substituted with one or more hydroxyl group(s);
wherein the overall charge of the compounds of formula (Ib) is positive.

4. The method according to claim 1, wherein $Y^+$ is chosen from the compounds of formula (Ic) wherein:
R'$_1$ and R'$_2$ are independently chosen from a hydrogen atom or a linear or branched ($C_1$-$C_4$)alkyl group, optionally substituted with one or more groups chosen from hydroxyl, amino, ($C_1$-$C_6$)dialkylamino, ($C_1$-$C_6$)alkylamino, carboxyl, carboxylate, carbamide, ($C_1$-$C_4$)alkoxyl, —$SO_3H$, —$SO_3^-$, or phenyl; and
R'$_3$ is independently chosen from a group —C(O)OR'$_4$, a group —OC(O)—R'$_4$, a group —C(O)NHR'$_4$, or a group —NH—C(O)—R'$_4$;
R'$_4$ representing a ($C_1$-$C_{12}$)alkyl group, optionally substituted with one or more groups chosen from hydroxyl, amino, ($C_1$-$C_6$)dialkylamino, or ($C_1$-$C_6$)alkylamino;
wherein the overall charge of the compounds of formula (Ic) is positive.

5. The method according to claim 1, wherein $Y^+$ is chosen from the compounds of formula (Id), wherein:
R''$_1$ represents a linear or branched, saturated or unsaturated, unsubstituted $C_1$-$C_6$ hydrocarbon-based group; and
R''$_2$ is independently chosen from a hydroxyl group or a linear or branched, unsubstituted ($C_1$-$C_6$)alkyl group.

6. The method according to claim 1, wherein $Y^+$ is chosen from one or more of compounds 1 to 69:

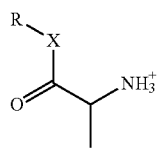
1

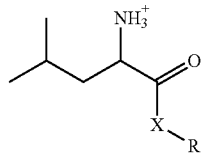
2

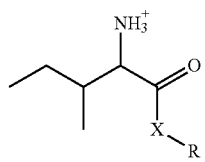
3

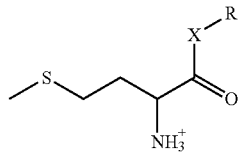
4

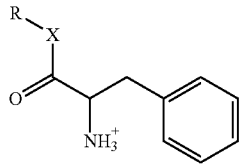
5

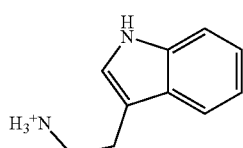
6

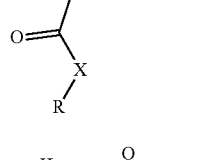
7

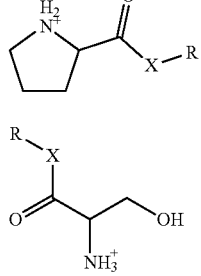
8

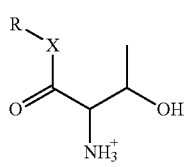
9

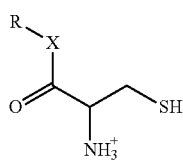
10

11
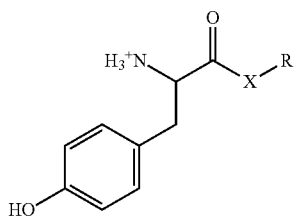
12
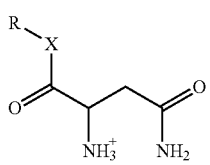
13
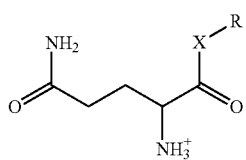
14
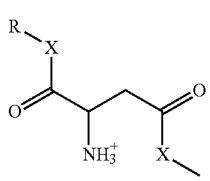
15
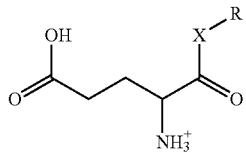
16
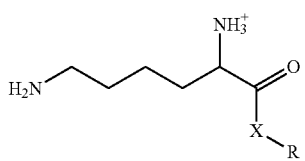
17
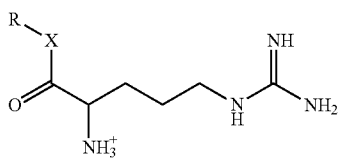
18
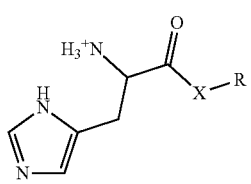
19
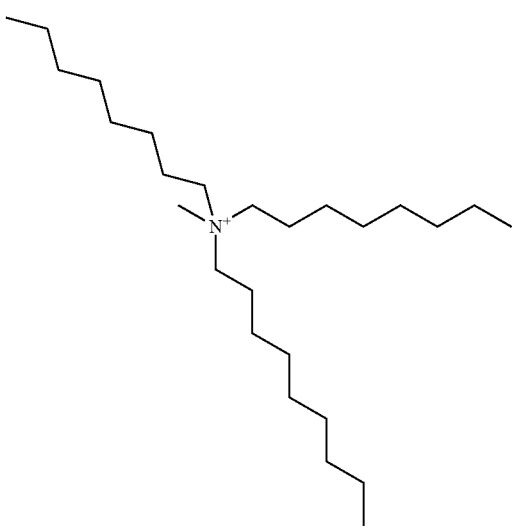
20
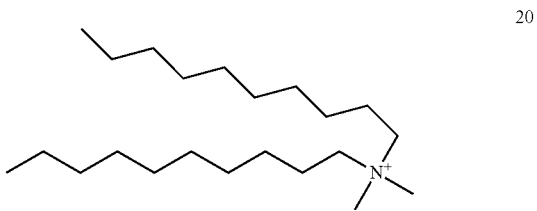
21
22
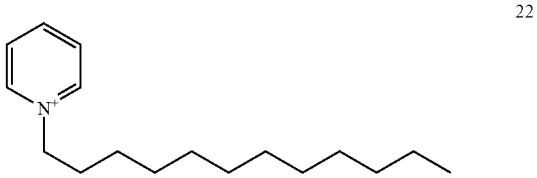
23
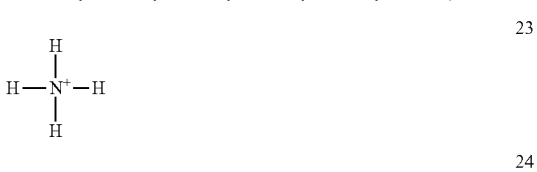
24
25

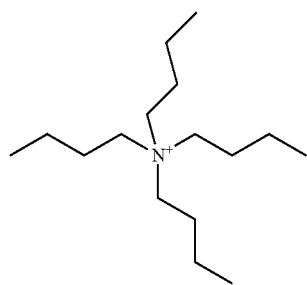
26
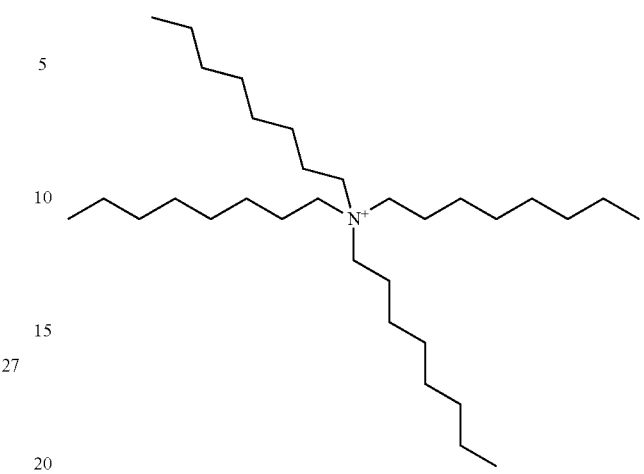
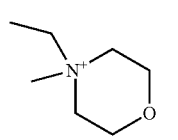
27
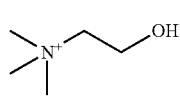
28
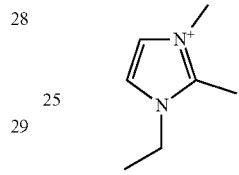
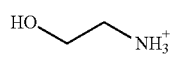
29
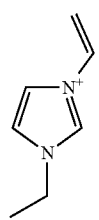
30
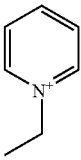
30
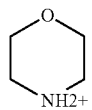
31
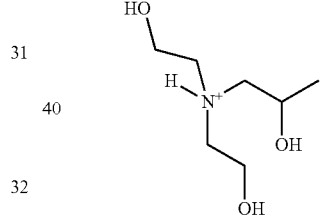
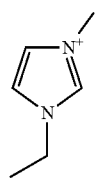
32
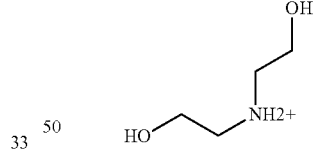
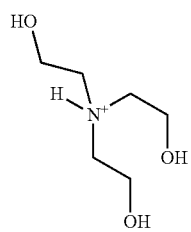
33
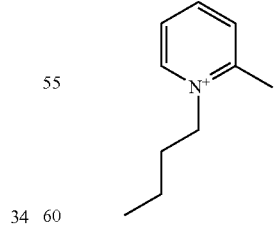
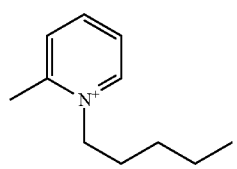
34
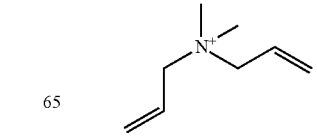

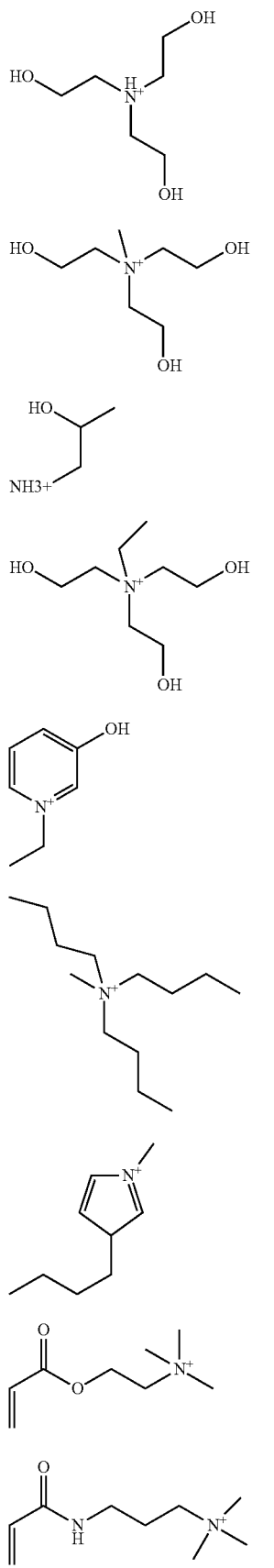
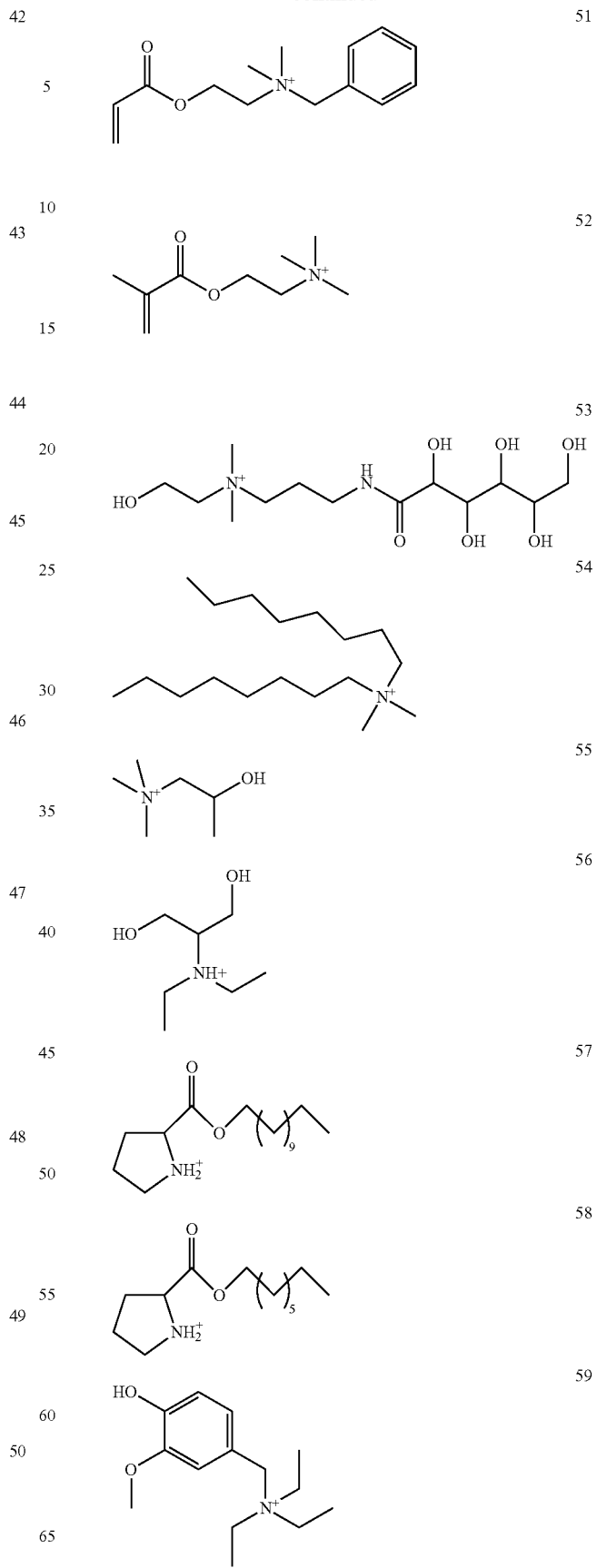

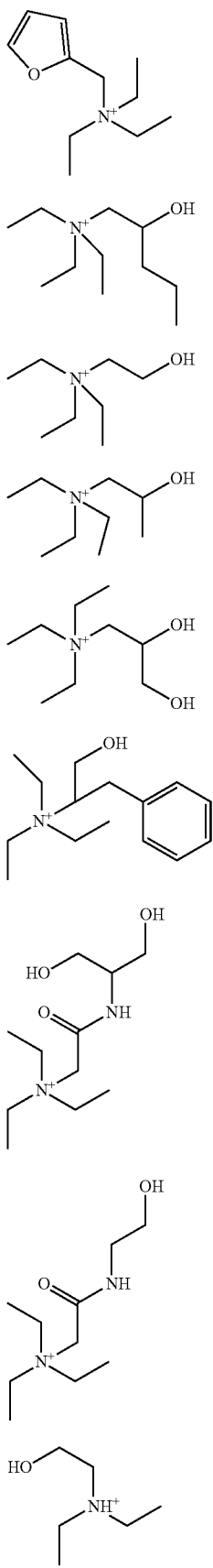

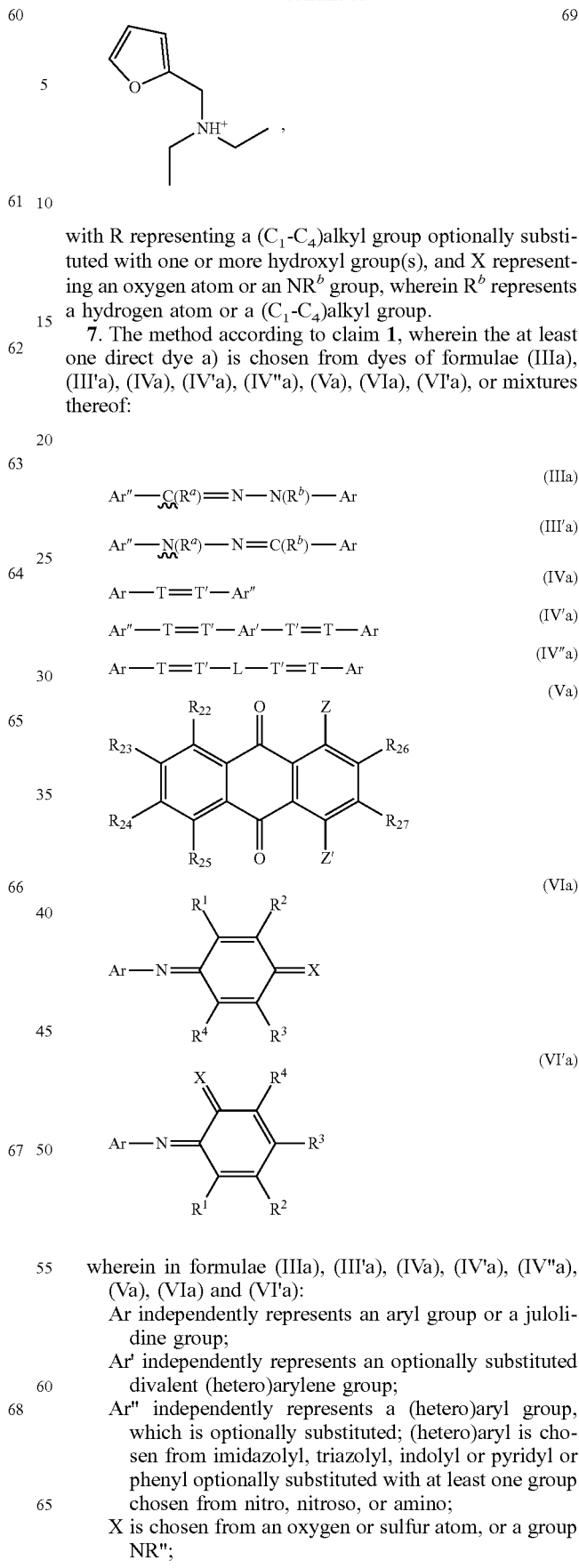

with R representing a $(C_1-C_4)$alkyl group optionally substituted with one or more hydroxyl group(s), and X representing an oxygen atom or an $NR^b$ group, wherein $R^b$ represents a hydrogen atom or a $(C_1-C_4)$alkyl group.

7. The method according to claim 1, wherein the at least one direct dye a) is chosen from dyes of formulae (IIIa), (III'a), (IVa), (IV'a), (IV"a), (Va), (VIa), (VI'a), or mixtures thereof:

wherein in formulae (IIIa), (III'a), (IVa), (IV'a), (IV"a), (Va), (VIa) and (VI'a):
- Ar independently represents an aryl group or a julolidine group;
- Ar' independently represents an optionally substituted divalent (hetero)arylene group;
- Ar" independently represents a (hetero)aryl group, which is optionally substituted; (hetero)aryl is chosen from imidazolyl, triazolyl, indolyl or pyridyl or phenyl optionally substituted with at least one group chosen from nitro, nitroso, or amino;
- X is chosen from an oxygen or sulfur atom, or a group NR";

R$^1$, R$^2$, R$^3$ and R$^4$ are independently chosen from a hydrogen or halogen atom, or a group chosen from hydroxyl, thiol, (C$_1$-C$_4$)alkyl, (C$_1$-C$_4$)alkoxy, (di)(C$_1$-C$_4$)(alkyl)amino, nitro, or nitroso;

R$^a$ and R$^b$ are independently chosen from a hydrogen atom or a (C$_1$-C$_8$)alkyl group;

or, as a variant, the substituent R$^a$ with a substituent of Ar'' and/or R$^b$ with a substituent of Ar and/or R$^a$ with R$^b$ form, together with the atoms that bear them, a (hetero)cycloalkyl;

T and T' are independently chosen from a group C(R$^a$) or N; and

L represents a divalent group -ALK-, —C(X)-ALK-, -ALK-C(X)—, or —C(X)-ALK-C(X')— with ALK representing a linear or branched (C$_1$-C$_6$)alkylene group;

R$_{22}$, R$_{23}$, R$_{24}$, R$_{25}$, R$_{26}$ and R$_{27}$ are independently chosen from a hydrogen or halogen atom, or a group chosen from:

(C$_1$-C$_6$)alkyl;

hydroxyl or mercapto;

(C$_1$-C$_6$)alkoxy or (C$_1$-C$_6$)alkylthio;

aryloxy or arylthio;

aryl(C$_1$-C$_6$)(alkyl)amino;

(di)(C$_1$-C$_6$)(alkyl)amino; or (di)(hydroxy(C$_1$-C$_6$)alkyl)amino;

Z' represents a hydrogen atom or a group NR$_{28}$R$_{29}$ with R$_{28}$ and R$_{29}$ independently chosen from a hydrogen atom or a group chosen from:

(C$_1$-C$_6$)alkyl;

polyhydroxy(C$_1$-C$_6$)alkyl;

aryl optionally substituted with one or more groups; or cycloalkyl; and

Z represents a group chosen from hydroxyl or NR'$_{28}$R'$_{29}$ with R'$_{28}$ and R'$_{29}$ independently chosen from the same atoms or groups as R$_{28}$ and R$_{29}$ as defined above.

8. The method according to claim 1, wherein the at least one direct dye a) is a neutral direct dye chosen from the following compounds (A) to (G) or mixtures thereof:

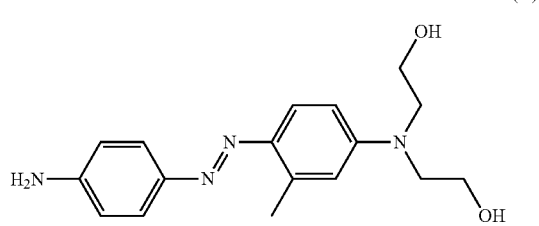
(A)

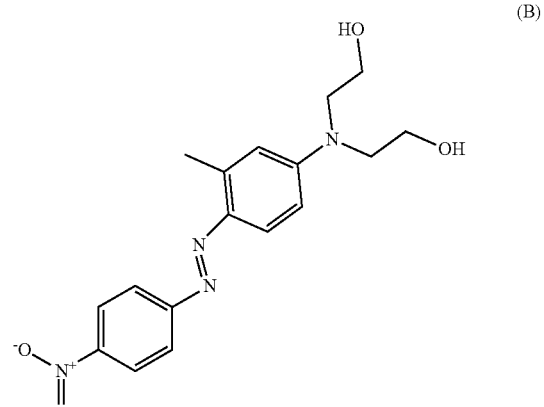
(B)

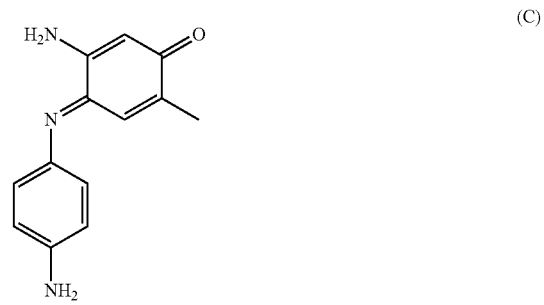
(C)

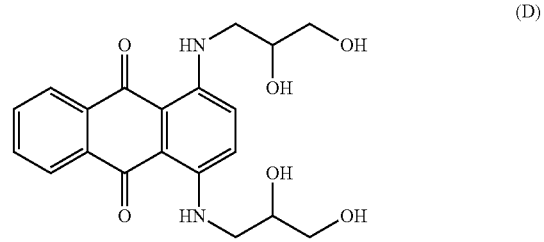
(D)

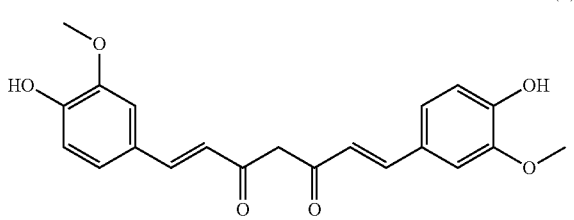
(E)

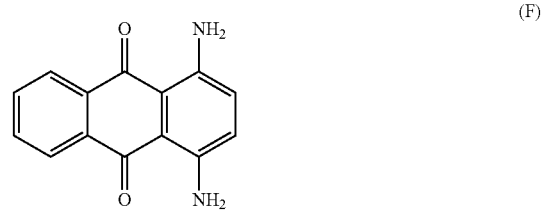
(F)

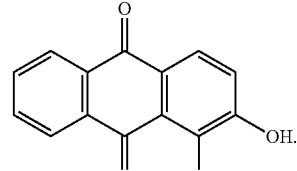
(G)

9. The method according to claim 1, wherein the at least one direct dye a) is an anionic direct dye chosen from the dyes of formulae (III), (III'), (IV), (IV'), (V), (V'), (VI), (VI'), (VII), (VIII), (IX), (X), or mixtures thereof:

a) the diaryl anionic azo dyes of formula (III) or (III'):

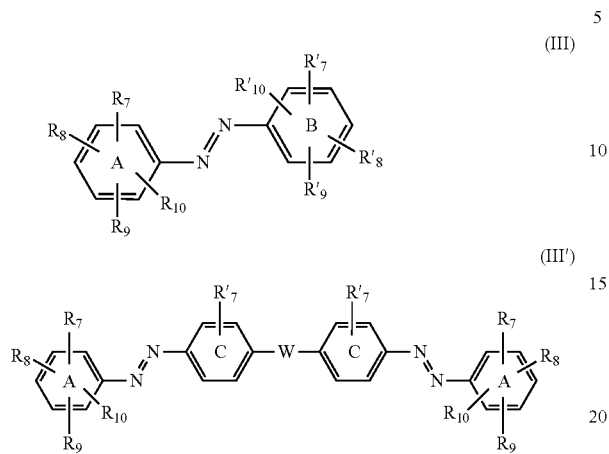

wherein in formulae (III) and (III'):

$R_7$, $R_8$, $R_9$, $R_{10}$, $R'_7$, $R'_8$, $R'_9$ and $R'_{10}$ are independently chosen from a hydrogen atom or a group chosen from:

($C_1$-$C_6$)alkyl;

($C_1$-$C_6$)alkoxy or ($C_1$-$C_6$)alkylthio;

hydroxyl or mercapto;

nitro or nitroso;

$R^o$—C(X)—X'—, $R^o$—X'—C(X)—, or $R^o$—X'—C(X)—X"— with $R^o$ representing a hydrogen atom or a ($C_1$-$C_6$)alkyl or aryl group; X, X' and X" independently chosen from an oxygen or sulfur atom, or NR with R representing a hydrogen atom or a ($C_1$-$C_6$)alkyl group;

$(O)_2S(O^-)$—, $M^+$ with $M^+$ representing a hydrogen atom or a cationic counterion;

$(O)CO^-$—, $M^+$ with $M^+$ representing a hydrogen atom or a cationic counterion;

R"—$S(O)_2$—, with R" representing a hydrogen atom, an alkyl group, or an aryl, (di)($C_1$-$C_6$)(alkyl)amino, or aryl($C_1$-$C_6$)(alkyl)amino group;

R"'—$S(O)_2$—X'— with R"' representing a ($C_1$-$C_6$) alkyl group or an aryl group which is optionally substituted, X' as defined above;

(di)($C_1$-$C_6$)(alkyl)amino;

aryl($C_1$-$C_6$)(alkyl)amino optionally substituted with one or more group(s) chosen from i) nitro; ii) nitroso; iii) $(O)_2S(O^-)$—, $M^+$ and iv) ($C_1$-$C_6$) alkoxy with $M^+$ representing a hydrogen atom or a cationic counterion;

optionally substituted heteroaryl;

cycloalkyl;

Ar—N=N— with Ar representing an optionally substituted aryl group;

or else two contiguous groups $R_7$ with $R_8$ or $R_8$ with $R_9$ or $R_9$ with $R_{10}$ together form a fused benzo group A'; and $R'_7$ with $R'_8$ or $R'_8$ with $R'_9$ or $R'_9$ with $R'_{10}$ together form a fused benzo group B'; with A' and B' optionally substituted with one or more group(s) chosen from i) nitro; ii) nitroso; iii) $(O)_2S(O^-)$—, $M^+$; iv) hydroxyl; v) mercapto; vi) (di)(alkyl)amino; vii) $R^o$—C(X)—X'—; viii) $R^o$—X'—C(X)—; ix) $R^o$—X'—C(X)—X"—; or x) Ar—N=N— and optionally substituted aryl ($C_1$-$C_6$)(alkyl)amino with $M^+$, $R^o$, X, X', X" and Ar as defined above; and W represents a sigma bond, an oxygen or sulfur atom, or a divalent group i) —NR— with R as defined above, or ii) methylene —C($R_a$)($R_b$)— with $R_a$ and $R_b$, independently chosen from a hydrogen atom or an aryl group, or alternatively $R_a$ and $R_b$ together form, with the carbon atom that bears them, a spiro cycloalkyl;

wherein formulae (III) and (III') comprise, on one of the rings A, A', B, B' or C:

at least one group $(O)_2S(O^-)$—, $M'^+$ with $M'^+$ representing a cationic counterion; or at least one group $(O)CO^-$—, $M'^+$ with $M'^+$ representing a cationic counterion;

b) the pyrazolone anionic azo dyes of formula (IV) or (IV'):

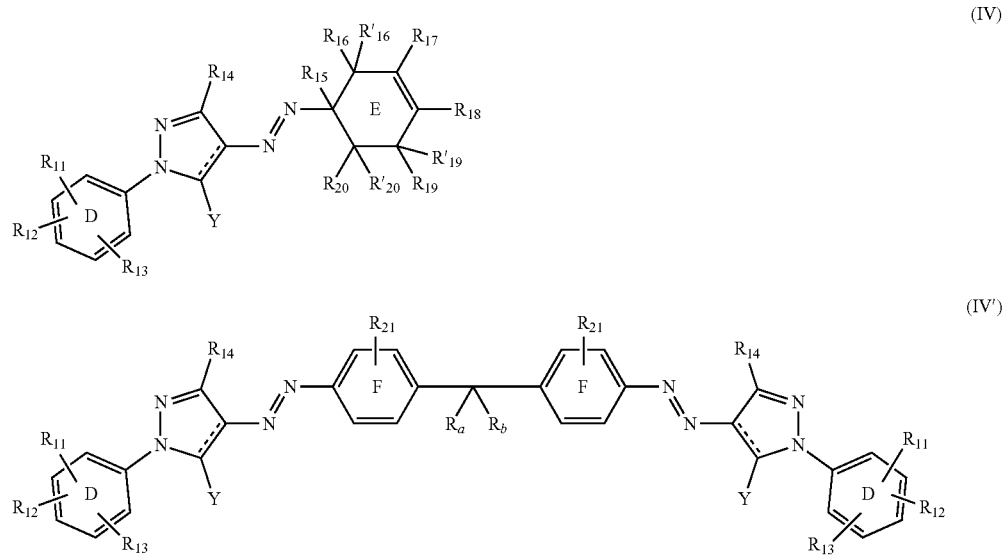

wherein in formulae (IV) and (IV')
- $R_{11}$, $R_{12}$ and $R_{13}$ are independently chosen from a hydrogen or halogen atom, a ($C_1$-$C_6$)alkyl group, or —(O)$_2$S(O$^-$), M$^+$ with M$^+$ representing a hydrogen atom or a cationic counterion;
- $R_{14}$ represents a hydrogen atom, a ($C_1$-$C_6$)alkyl group, or a —C(O)O$^-$, M$^+$ group with M$^+$ representing a hydrogen atom or a cationic counterion;
- $R_{15}$ represents a hydrogen atom;
- $R_{16}$ represents an oxo group when R'$_{16}$ is absent, or $R_{15}$ with $R_{16}$ together form a double bond;
- $R_{17}$ and $R_{18}$ are independently chosen from a hydrogen atom or a group chosen from:
  - (O)$_2$S(O$^-$)—, M$^+$ with M$^+$ representing a hydrogen atom or a cationic counterion; or
  - Ar—O—S(O)$_2$— with Ar representing an optionally substituted aryl group;
- $R_{19}$ and $R_{20}$ together form either a double bond or a benzo group D', which is optionally substituted;
- R'$_{16}$, R'$_{19}$ and R'$_{20}$ are independently chosen from a hydrogen atom, a ($C_1$-$C_6$)alkyl group, or a hydroxyl group;
- $R_{21}$ represents a hydrogen atom or a ($C_1$-$C_6$)alkyl or ($C_1$-$C_6$)alkoxy group;
- Y represents either a hydroxyl group or an oxo group; and
- ⋯ represents a single bond when Y is an oxo group; and represents a double bond when Y represents a hydroxyl group;

wherein formulae (IV) and (IV') comprise, on one of the rings D or E:
- at least one group (O)$_2$S(O$^-$)—, M'$^+$ with M'$^+$ representing a cationic counterion; or
- at least one group (O)CO$^-$—, M'$^+$ with M'$^+$ representing a cationic counterion;

c) the anthraquinone dyes of formulae (V) and (V'):

(V)

(V')

wherein in formulae (V) and (V'):
- $R_{22}$, $R_{23}$, $R_{24}$, $R_{25}$, $R_{26}$ and $R_{27}$ are independently chosen from a hydrogen or halogen atom, or a group chosen from:
  - ($C_1$-$C_6$)alkyl;
  - hydroxyl or mercapto;
  - ($C_1$-$C_6$)alkoxy or ($C_1$-$C_6$)alkylthio;
  - optionally substituted aryloxy or arylthio;
  - aryl($C_1$-$C_6$)(alkyl)amino optionally substituted with one or more groups chosen from alkyl or (O)$_2$S(O$^-$)—, M$^+$ with M$^+$ representing a hydrogen atom or a cationic counterion;
  - (di)($C_1$-$C_6$)(alkyl)amino;
  - (di)(hydroxy($C_1$-$C_6$)alkyl)amino; or
  - (O)$_2$S(O$^-$)—, M$^+$ with M$^+$ representing a hydrogen atom or a cationic counterion;
- Z' represents a hydrogen atom or a group NR$_{28}$R$_{29}$ with $R_{28}$ and $R_{29}$ independently chosen from a hydrogen atom or a group chosen from:
  - ($C_1$-$C_6$)alkyl;
  - polyhydroxy($C_1$-$C_6$)alkyl;
  - aryl optionally substituted with one or more groups; or
  - cycloalkyl; and
- Z represents a group chosen from hydroxyl or NR'$_{28}$R'$_{29}$ with R'$_{28}$ and R'$_2$ independently chosen from the same atoms or groups as $R_{28}$ and $R_{29}$ as defined above;

wherein formulae (V) and (V') comprise:
- at least one group (O)$_2$S(O$^-$)—, M'$^+$ with M'$^+$ representing a cationic counterion; or
- at least one group (O)CO$^-$—, M'$^+$ with M'$^+$ representing a cationic counterion;

d) the nitro dyes of formula (VI) or (VI'):

(VI)

(VI')

wherein in formulae (VI) and (VI'):
- $R_{30}$, $R_{31}$ and $R_{32}$ are independently chosen from a hydrogen or halogen atom, or a group chosen from:
  - ($C_1$-$C_6$)alkyl;
  - ($C_1$-$C_6$)alkoxy optionally substituted with one or more hydroxyl groups or ($C_1$-$C_6$)alkylthio optionally substituted with one or more hydroxyl group(s);
  - hydroxyl or mercapto;
  - nitro or nitroso;
  - polyhalo($C_1$-$C_6$)alkyl;
  - R°—C(X)—X'—, R°—X'—C(X)—, or R°—X'—C(X)—X"— with R°, X, X' and X" as defined above;

(O)₂S(O⁻)—, M⁺ with M⁺ representing a hydrogen atom or a cationic counterion;
(O)CO⁻—, M⁺ with M⁺ representing a hydrogen atom or a cationic counterion;
(di)($C_1$-$C_6$)(alkyl)amino;
(di)(hydroxy($C_1$-$C_6$)alkyl)amino; or
heterocycloalkyl;
$R_c$ and $R_d$ are independently chosen from a hydrogen atom or a ($C_1$-$C_6$)alkyl group;
ALK represents a linear or branched divalent $C_1$-$C_6$ alkylene group;
n is 1 or 2;
p represents an integer ranging from 1 to 5, inclusive;
q represents an integer ranging from 1 to 4, inclusive;
u is 0 or 1;
when n is 1, J represents a nitro or nitroso group;
when n is 2, J represents an oxygen or sulfur atom, or a divalent group —S(O)$_m$— with m representing an integer 1 or 2;
M" represents a hydrogen atom or a cationic counterion; and

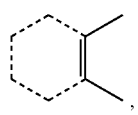

which may be present or absent, represents a benzo group optionally substituted with one or more groups $R_{30}$ as defined above;
wherein formulae (VI) and (VI') comprise:
at least one group (O)₂S(O⁻)—, M'⁺ with M'⁺ representing a cationic counterion; or
at least one group (O)CO⁻—, M'⁺ with M'⁺ representing a cationic counterion;
e) the triarylmethane dyes of formula (VII):

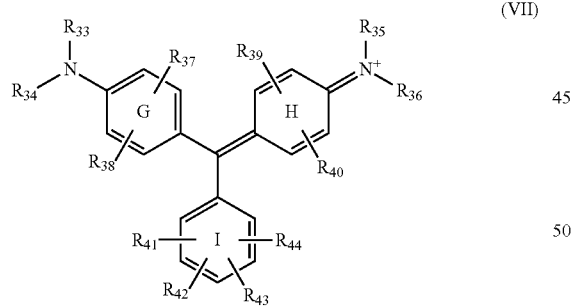

(VII)

wherein in formula (VII):
$R_{33}$, $R_{34}$, $R_{35}$ and $R_{36}$ are independently chosen from a hydrogen atom or a group chosen from ($C_1$-$C_6$)alkyl, optionally substituted aryl, optionally substituted aryl($C_1$-$C_6$)alkyl; and
$R_{37}$, $R_{38}$, $R_{39}$, $R_{40}$, $R_{41}$, $R_{42}$, $R_{43}$ and $R_{44}$ are independently chosen from a hydrogen atom or a group chosen from:
($C_1$-$C_6$)alkyl;
($C_1$-$C_6$)alkoxy or ($C_1$-$C_6$)alkylthio;
(di)($C_1$-$C_6$)(alkyl)amino;
hydroxyl or mercapto;
nitro or nitroso;
R°—C(X)—X'—, R°—X'—C(X)—, or R°—X'—C(X)—X"— with R° representing a hydrogen atom or an alkyl or aryl group; X, X' and X" independently chosen from an oxygen or sulfur atom, or NR with R representing a hydrogen atom or a ($C_1$-$C_6$)alkyl group;
(O)₂S(O⁻)—, M⁺ with M⁺ representing a hydrogen atom or a cationic counterion;
(O)CO⁻—, M⁺ with M⁺ representing a hydrogen atom or a cationic counterion;
or two contiguous groups $R_{41}$ with $R_{42}$ or $R_{42}$ with $R_{43}$ or $R_{43}$ with $R_{44}$ together form a fused benzo group optionally substituted with one or more group(s) chosen from:
i) nitro;
ii) nitroso;
iii) (O)₂S(O⁻)—, M⁺;
iv) hydroxyl;
v) mercapto;
vi) (di)($C_1$-$C_6$)(alkyl)amino;
vii) R°—C(X)—X'—;
viii) R°—X'—C(X)—; or
ix) R°—X'—C(X)—X"—;
with M⁺, R°, X, X' and X" as defined above;
wherein at least one of the rings G, H, or I comprises:
at least one group (O)₂S(O⁻)—, M'⁺ with M'⁺ representing a cationic counterion; or
at least one group (O)CO⁻—, M'⁺ with M'⁺ representing a cationic counterion;
f) the xanthene-based dyes of formula (VIII):

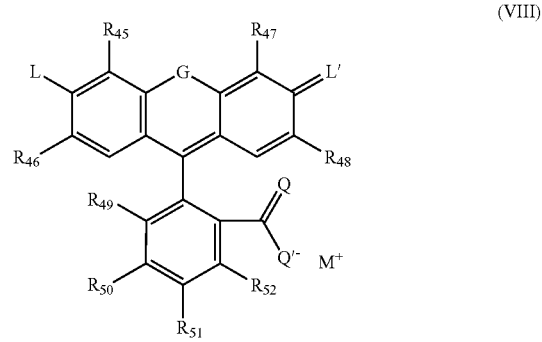

(VIII)

wherein in formula (VIII):
$R_{45}$, $R_{46}$, $R_{47}$ and $R_{48}$ are independently chosen from a hydrogen atom or a halogen atom;
$R_{49}$, $R_{50}$, $R_{51}$ and $R_{52}$ are independently chosen from a hydrogen or halogen atom, or a group chosen from:
($C_1$-$C_6$)alkyl;
($C_1$-$C_6$)alkoxy or ($C_1$-$C_6$)alkylthio;
hydroxyl or mercapto;
nitro or nitroso;
(O)₂S(O⁻)—, M⁺ with M⁺ representing a hydrogen atom or a cationic counterion; or
(O)CO⁻—, M⁺ with M⁺ representing a hydrogen atom or a cationic counterion;
G represents an oxygen or sulfur atom;
L represents an alkoxide O⁻, M⁺; a thioalkoxide S⁻, M⁺ or a group NR$_f$, with R$_f$ representing a hydrogen atom or a ($C_1$-$C_6$)alkyl group, and M⁺ representing a hydrogen atom or a cationic counterion;
L' represents an oxygen or sulfur atom or an ammonium group: N⁺R$_f$R$_g$, with R$_f$ and R$_g$ independently chosen from a hydrogen atom, a $(C_1-C_6)$ alkyl group or an optionally substituted aryl group;

Q and Q' are independently chosen from an oxygen or sulfur atom; and $M^+$ represents a hydrogen atom or a cationic counterion;

g) the indole-based dyes of formula (IX):

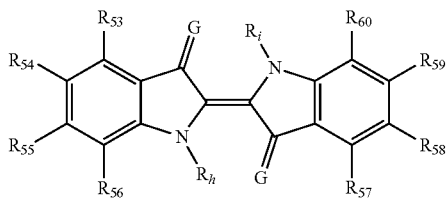

(IX)

wherein in formula (IX):

$R_{53}$, $R_{54}$, $R_{55}$, $R_{56}$, $R_{57}$, $R_{58}$, $R_{59}$ and $R_{60}$ are independently chosen from a hydrogen atom or a group chosen from:

$(C_1-C_6)$alkyl;

$(C_1-C_6)$alkoxy or $(C_1-C_6)$alkylthio;

hydroxyl or mercapto;

nitro or nitroso;

$R^o$—C(X)—X'—, $R^o$—X'—C(X)—, or $R^o$—X'—C(X)—X''— with $R^o$ representing a hydrogen atom or an alkyl or aryl group; X, X' and X'' independently chosen from an oxygen or sulfur atom, or NR with R representing a hydrogen atom or a $(C_1-C_6)$alkyl group;

$(O)_2S(O^-)$—, $M^+$ with $M^+$ representing a hydrogen atom or a cationic counterion; or $(O)CO^-$—, $M^+$ with $M^+$ representing a hydrogen atom or a cationic counterion;

G represents an oxygen or sulfur atom or a group $NR_e$ with $R_e$ as defined above; and $R_i$ and $R_h$ are independently chosen from a hydrogen atom or a $(C_1-C_6)$alkyl group;

wherein formula (IX) comprises:

at least one group $(O)_2S(O^-)$—, $M'^+$ with $M'^+$ representing a cationic counterion; or at least one group $(O)CO^-$—, $M'^+$ with $M'^+$ representing a cationic counterion;

h) the quinoline-based dyes of formula (X):

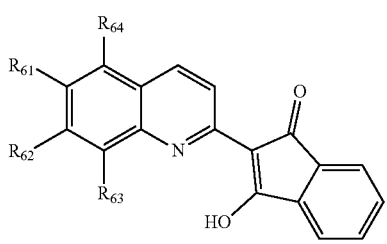

(X)

wherein in formula (X):

$R_{61}$ represents a hydrogen or halogen atom or a $(C_1-C_6)$alkyl group; and $R_{62}$, $R_{63}$ and $R_{64}$ are independently chosen from a hydrogen atom or a group $(O)_2S(O^-)$—, $M^+$ with $M^+$ representing a hydrogen atom or a cationic counterion;

or else $R_{61}$ with $R_{62}$, or $R_{61}$ with $R_{64}$, together form a benzo group optionally substituted with one or more groups $(O)_2S(O^-)$—, $M^+$ with $M^+$ representing a hydrogen atom or a cationic counterion;

wherein formula (X) comprises at least one group $(O)_2S(O^-)$—, $M'^+$ with $M'^+$ representing a cationic counterion.

10. The method according to claim 1, wherein the at least one direct dye has a solubility in water of less than 5% by weight at a temperature of 22° C. and at atmospheric pressure of 760 mmHg.

11. The method according to claim 1, wherein the method comprises applying a composition comprising the (a) at least one direct dye to the keratin fibers, and the total amount of direct dyes in the composition ranges from 0.001% to 10% by weight, relative to the weight of the composition.

12. The method according to claim 11, wherein the method comprises applying a composition comprising the (a) at least one direct dye to the keratin fibers, and the total amount of direct dyes in the composition ranges from 0.05% to 5% by weight, relative to the weight of the composition.

13. The method according to claim 1, wherein the method comprises applying a composition comprising the (a) at least one direct dye to the keratin fibers, and the total amount of direct dyes in the composition ranges from 0.3% to 3% by weight, relative to the weight of the composition.

14. The method according to claim 1, wherein the method comprises applying a composition comprising the (b) at least one compound of formula (A) to the keratin fibers, and the total amount of compounds of formula (A) in the composition ranges from 1% to 90% by weight, relative to the weight of the composition.

15. The method according to claim 1, wherein the method comprises applying a composition comprising the (b) at least one compound of formula (A) to the keratin fibers, and the total amount of compounds of formula (A) in the composition ranges from 10% to 80% by weight, relative to the weight of the composition.

16. The method according to claim 1, wherein the method comprises applying a composition comprising the (b) at least one compound of formula (A) to the keratin fibers, and the total amount of compounds of formula (A) in the composition ranges from 20% to 60% by weight, relative to the weight of the composition.

17. The method according to claim 1, wherein the method comprises applying the (b) at least one compound of formula (A) to the keratin fibers simultaneously with applying the (a) at least one direct dye to the keratin fibers, wherein the (b) at least one compound of formula (A) and the (a) at least one direct dye are in the same composition or in separate compositions.

18. The method according to claim 1, wherein the method comprises applying a composition comprising the (b) at least one compound of formula (A) to the keratin fibers before and/or after applying a composition comprising the (a) at least one direct dye to the keratin fibers.

19. A composition comprising:
(a) optionally at least one direct dye; and
(b) at least one compound of formula (A):

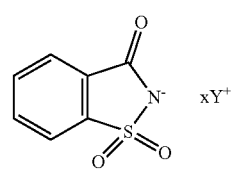

(A)

wherein:
Y⁺, which can be the same or different, represents a cationic counterion chosen from the compounds of formula (Ia), (Ib), (Ic) or (Id) below:

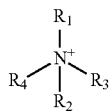

(Ia)

wherein in formula (Ia), $R_1$, $R_2$, $R_3$ and $R_4$ are independently chosen from:
a hydrogen atom; or
a linear or branched, saturated or unsaturated, $C_1$-$C_{12}$ hydrocarbon-based group, optionally: (i) substituted with one or more groups chosen from hydroxyl, thiol, ($C_1$-$C_6$)alkylthio, amino, —$NH_3^+$, ($C_1$-$C_6$)dialkylamino, ($C_1$-$C_6$)alkylamino, ($C_1$-$C_4$)alkoxyl, carboxyl, carboxylate, —$SO_3H$, —$SO_3^-$, —C(O)$NH_2$, —NHC(NH)—$NH_2$, —C(O)OR$^a$, —OC(O)—R$^a$, —C(O)NHR$^a$, —NH—C(O)—R$^a$, phenyl, indolyl, phenol, furan, guaiacol, imidazole, or guanine, or (ii) interrupted by one or more group(s) chosen from —C(O)—, —NR$^b$—, —C(NR$^b$)—, —OC(O)—, —C(O)O—, —C(O)NR$^b$— or —NR$^b$C(O)—, with:
R$^a$ representing a ($C_1$-$C_4$)alkyl group; and
R$^b$ representing a hydrogen atom or a ($C_1$-$C_4$)alkyl group;
wherein the overall charge of the compounds of formula (Ia) is positive;

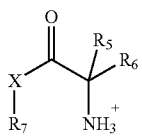

(Ib)

wherein in formula (Ib):
X represents an oxygen atom or an NR$^b$ group, with R$^b$ representing a hydrogen atom or a ($C_1$-$C_4$)alkyl group;
$R_5$, $R_6$ and $R_7$ represent independently of one another:
a hydrogen atom;
a carboxyl or carboxylate group;
a —C(O)$NH_2$ group; or
a linear or branched, saturated or unsaturated, $C_1$-$C_{12}$ hydrocarbon-based group, optionally: (i) substituted with one or more groups chosen from hydroxyl, thiol, ($C_1$-$C_6$)alkylthio, amino, —$NH_3^+$, ($C_1$-$C_6$)dialkylamino, ($C_1$-$C_6$)alkylamino, ($C_1$-$C_4$)alkoxyl, carboxyl, carboxylate, —$SO_3H$, —$SO_3^-$, —C(O)$NH_2$, —NHC(NH)—$NH_2$, —C(O)OR$^a$, —OC(O)—R$^a$, —C(O)NHR$^a$, —NH—C(O)—R$^a$, phenyl, indolyl, phenol, furan, guaiacol, imidazole, or guanine; or (ii) interrupted by one or more group(s) chosen from —C(O)—, —NR$^b$—, —C(NR$^b$)—, —OC(O)—, —C(O)O—, —C(O)NR$^b$— or —NR$^b$C(O)—, with:
R$^a$ representing a ($C_1$-$C_4$)alkyl group; and
R$^b$ representing a hydrogen atom or a ($C_1$-$C_4$)alkyl group;

wherein the overall charge of the compounds of formula (Ib) is positive;

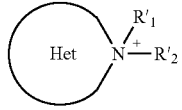

(Ic)

wherein in formula (Ic):
Het represents a cationic saturated heterocyclic group comprising:
from 5 to 10 ring members; and
in addition to the ammonium bearing R'$_1$ and R'$_2$, optionally also bearing one or two atoms chosen from nitrogen and/or oxygen atoms;
the heterocyclic group being optionally substituted with one or more groups R'$_3$, which is independently chosen from a hydroxyl group, an amino group, a —C(O)OR'4 group, an —OC(O)—R'4 group, a —C(O)NHR'4 group, an —NH—C(O)—R'4 group, a linear or branched, saturated or unsaturated, C1-C12 hydrocarbon-based group, optionally substituted with one or more groups chosen from: hydroxyl, amino, (C1-C6)dialkylamino, (C1-C6)alkylamino, carboxyl, carboxylate, carbamide, (C1-C4)alkoxyl, —SO3H, —SO3⁻, or phenyl;
R'4 represents a hydrogen atom, a linear or branched, saturated or unsaturated, C1-C12 hydrocarbon-based group, optionally substituted with one or more groups chosen from hydroxyl, amino, (C1-C6)dialkylamino or (C1-C6)alkylamino; and
R'$_1$ and R'$_2$ are independently chosen from a hydrogen atom or a linear or branched, saturated or unsaturated, $C_1$-$C_{12}$ hydrocarbon-based group, optionally substituted with one or more groups chosen from hydroxyl, amino, ($C_1$-$C_6$)dialkylamino, ($C_1$-$C_6$)alkylamino, carboxyl, carboxylate, carbamide, ($C_1$-$C_4$)alkoxyl, —$SO_3H$, —$SO_3^-$, or phenyl;
wherein the overall charge of the compounds of formula (Ic) is positive;

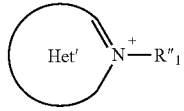

(Id)

wherein in formula (Id):
Het' represents a cationic aromatic unsaturated heterocyclic group comprising:
from 5 to 10 ring members; and
in addition to the ammonium bearing R"$_1$, optionally also bearing one or two atoms chosen from nitrogen and/or oxygen atoms;
the heterocyclic group being optionally substituted with one or more groups R"$_2$, which is independently chosen from a hydroxyl group, an amino group, or a linear or branched, saturated or unsaturated, $C_1$-$C_{12}$ hydrocarbon-based group, optionally substituted with one or more group(s) chosen from hydroxyl, amino, ($C_1$-$C_6$)dialkylamino, ($C_1$-$C_6$)alkylamino, carboxyl, carboxylate, carbamide, ($C_1$-$C_4$)alkoxyl, —$SO_3H$, —$SO_3^-$ or phenyl; and R''$_1$ represents a linear or branched, saturated or unsaturated, $C_1$-$C_{12}$ hydrocarbon-based group, optionally substituted with one or more groups chosen from hydroxyl, amino, ($C_1$-$C_6$)dialkylamino, ($C_1$-$C_6$)alkylamino, carboxyl, carboxylate, carbamide, ($C_1$-$C_4$)alkoxyl, —SO$_3$H, —SO$_3$$^-$, or phenyl;

wherein the overall charge of the compounds of formula (Id) is positive; and x is a stoichiometric coefficient configured to balance the electrical neutrality of the compound of formula (A);

wherein the ingredients a) and b) are applied simultaneously or sequentially to the keratin fibers.

20. A multicompartment kit comprising:

i. a first compartment comprising at least one direct dye, and ii. a second compartment comprising at least one compound of formula (A):

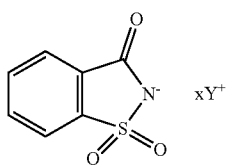

(A)

wherein:

Y$^+$, which can be the same or different, represents a cationic counterion chosen from compounds of formula (Ia), (Ib), (Ic), and/or (Id) below:

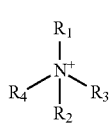

(Ia)

wherein in formula (Ia), $R_1$, $R_2$, $R_3$ and $R_4$ are independently chosen from:

a hydrogen atom; and/or a linear or branched, saturated or unsaturated, $C_1$-$C_{12}$ hydrocarbon-based group, optionally: (i) substituted with one or more groups chosen from hydroxyl, thiol, ($C_1$-$C_6$)alkylthio, amino, —NH$_3$$^+$, ($C_1$-$C_6$)dialkylamino, ($C_1$-$C_6$)alkylamino, ($C_1$-$C_4$)alkoxyl, carboxyl, carboxylate, —SO$_3$H, —SO$_3$$^-$, —C(O)NH$_2$, —NHC(NH)—NH$_2$, —C(O)OR$^a$, —OC(O)—R$^a$, —C(O)NHR$^a$, —NH—C(O)—R$^a$, phenyl, indolyl, phenol, furan, guaiacol, imidazole, or guanine; or (ii) interrupted by one or more group(s) chosen from —C(O)—, —NR$^b$—, —C(NR$^b$)—, —OC(O)—, —C(O)O—, —C(O)NR$^b$— or —NR$^b$C(O)—, with:

R$^a$ representing a ($C_1$-$C_4$)alkyl group; and

R$^b$ representing a hydrogen atom or a ($C_1$-$C_4$)alkyl group;

wherein the overall charge of the compounds of formula (Ia) is positive;

(Ib)

wherein in formula (Ib):

X represents an oxygen atom or an NR$^b$ group, R$^b$ representing a hydrogen atom or a ($C_1$-$C_4$)alkyl group;

$R_5$, $R_6$ and $R_7$ represent independently of one another:

a hydrogen atom;

a carboxyl or carboxylate group;

a —C(O)NH$_2$ group; and/or a linear or branched, saturated or unsaturated, $C_1$-$C_{12}$ hydrocarbon-based group, optionally: (i) substituted with one or more groups chosen from hydroxyl, thiol, ($C_1$-$C_6$)alkylthio, amino, —NH$_3$$^+$, ($C_1$-$C_6$)dialkylamino, ($C_1$-$C_6$)alkylamino, ($C_1$-$C_4$)alkoxyl, carboxyl, carboxylate, —SO$_3$H, —SO$_3$$^-$, —C(O)NH$_2$, —NHC(NH)—NH$_2$, —C(O)OR$^a$, —OC(O)—R$^a$, —C(O)NHR$^a$, —NH—C(O)—R$^a$, phenyl, indolyl, phenol, furan, guaiacol, imidazole, or guanine; or (ii) interrupted by one or more group(s) chosen from —C(O)—, —NR$^b$—, —C(NR$^b$)—, —OC(O)—, —C(O)O—, —C(O)NR$^b$— or —NR$^b$C(O)—, with:

R$^a$ representing a ($C_1$-$C_4$)alkyl group; and

R$^b$ representing a hydrogen atom or a ($C_1$-$C_4$)alkyl group;

wherein the overall charge of the compounds of formula (Ib) is positive;

(Ic)

wherein in formula (Ic):

Het represents a cationic saturated heterocyclic group comprising:

from 5 to 10 ring members; and in addition to the ammonium bearing R'$_1$ and R'$_2$, optionally also bearing one or two atoms chosen from nitrogen and/or oxygen atoms;

the heterocyclic group being optionally substituted with one or more groups R'$_3$, which is independently chosen from a hydroxyl group, an amino group, a —C(O)OR'$_4$ group, an —OC(O)—R'$_4$ group, a —C(O)NHR'$_4$ group, an —NH—C(O)—R'$_4$ group, a linear or branched, saturated or unsaturated, $C_1$-$C_{12}$ hydrocarbon-based group, optionally substituted with one or more groups chosen from: hydroxyl, amino, ($C_1$-$C_6$)dialkylamino, ($C_1$-$C_6$)alkylamino, carboxyl, carboxylate, carbamide, ($C_1$-$C_4$)alkoxyl, —SO$_3$H, —SO$_3$$^-$ or phenyl;

R'₄ representing a hydrogen atom, a linear or branched, saturated or unsaturated, $C_1$-$C_{12}$ hydrocarbon-based group, optionally substituted with one or more groups chosen from hydroxyl, amino, ($C_1$-$C_6$)dialkylamino or ($C_1$-$C_6$)alkylamino; and R'₁ and R'₂ are independently chosen from a hydrogen atom or a linear or branched, saturated or unsaturated, $C_1$-$C_{12}$ hydrocarbon-based group, optionally substituted with one or more groups chosen from hydroxyl, amino, ($C_1$-$C_6$)dialkylamino, ($C_1$-$C_6$)alkylamino, carboxyl, carboxylate, carbamide, ($C_1$-$C_4$)alkoxyl, —SO₃H, —SO₃⁻, or phenyl;

wherein the overall charge of the compounds of formula (Ic) is positive;

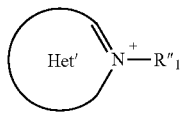

(Id)

wherein in formula (Id):

Het' represents a cationic aromatic unsaturated heterocyclic group comprising:
from 5 to 10 ring members; and
in addition to the ammonium bearing R"₁, optionally also bearing one or two atoms chosen from nitrogen and/or oxygen atoms;
said heterocyclic group being optionally substituted with one or more groups R"₂ which is independently chosen from a hydroxyl group, an amino group, or a linear or branched, saturated or unsaturated, C1-C12 hydrocarbon-based group, optionally substituted with one or more group(s) chosen from hydroxyl, amino, (C1-C6)dialkylamino, (C1-C6)alkylamino, carboxyl, carboxylate, carbamide, (C1-C4)alkoxyl, —SO3H, —SO3⁻, or phenyl; and R"₁ represents a linear or branched, saturated or unsaturated, $C_1$-$C_{12}$ hydrocarbon-based group, optionally substituted with one or more groups chosen from hydroxyl, amino, ($C_1$-$C_6$)dialkylamino, ($C_1$-$C_6$)alkylamino, carboxyl, carboxylate, carbamide, ($C_1$-$C_4$)alkoxyl, —SO₃H, —SO₃⁻, or phenyl;

wherein the overall charge of the compounds of formula (Id) is positive; and x is a stoichiometric coefficient configured to balance the electrical neutrality of the compound of formula (A).

* * * * *